(12) United States Patent
Hershey et al.

(10) Patent No.: US 11,135,438 B2
(45) Date of Patent: Oct. 5, 2021

(54) METHODS AND SYSTEMS FOR STIMULATION FOR GLIAL MODULATION

(71) Applicant: Boston Scientific Neuromodulation Corporation, Valencia, CA (US)

(72) Inventors: Bradley Lawrence Hershey, Carrollton, TX (US); Tianhe Zhang, Studio City, CA (US); Natalie A. Brill, Sherman Oaks, CA (US); Rosana Esteller, Santa Clarita, CA (US); Jianwen Gu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 170 days.

(21) Appl. No.: 16/242,461

(22) Filed: Jan. 8, 2019

(65) Prior Publication Data

US 2019/0209849 A1 Jul. 11, 2019

Related U.S. Application Data

(60) Provisional application No. 62/616,360, filed on Jan. 11, 2018.

(51) Int. Cl.
*A61N 1/37* (2006.01)
*A61N 1/372* (2006.01)
*A61N 1/36* (2006.01)

(52) U.S. Cl.
CPC ..... *A61N 1/37247* (2013.01); *A61N 1/36062* (2017.08); *A61N 1/36185* (2013.01)

(58) Field of Classification Search
CPC ............ A61N 1/37247; A61N 1/36062; A61N 1/36185

(Continued)

(56) References Cited

U.S. PATENT DOCUMENTS 5,076,270 A 12/1991 Stutz, Jr.
5,437,193 A 8/1995 Schleitweiler et al.
(Continued)

FOREIGN PATENT DOCUMENTS

WO 02/091935 11/2002
WO 2011/031131 3/2011
(Continued)

OTHER PUBLICATIONS

International Search Report and Written Opinion for PCT Application No. PCT/US2019/012652 dated Jul. 3, 2019.
(Continued)

*Primary Examiner* — Carl H Layno
*Assistant Examiner* — Michael J Lau
(74) *Attorney, Agent, or Firm* — Branch Partners PLLC; Bruce E. Black

(57) ABSTRACT

A system for planning or conducting stimulation includes a display; and a processor that executes instructions configured for: displaying, on the display, a representation of a stimulation effect; obtaining and displaying, on the display, a path for migration of the stimulation effect; receiving a duration or rate for migration of the stimulation effect; and determining a selection of one or more electrodes or optical stimulators for one or more stimulation leads of a stimulation system to produce the stimulation effect and conduct the migration of the stimulation effect along the path according to the duration or rate.

20 Claims, 15 Drawing Sheets

(58) Field of Classification Search
USPC .......................................................... 607/3
See application file for complete search history.

(56) References Cited

U.S. PATENT DOCUMENTS

| | | | |
|---|---|---|---|
| 5,445,608 | A | 8/1995 | Chen et al. |
| 5,556,421 | A | 9/1996 | Prutchi et al. |
| 6,052,624 | A | 4/2000 | Mann |
| 6,175,710 | B1 | 1/2001 | Kamaji et al. |
| 6,181,969 | B1 | 1/2001 | Gord |
| 6,224,450 | B1 | 5/2001 | Norton |
| 6,271,094 | B1 | 8/2001 | Boyd et al. |
| 6,295,944 | B1 | 10/2001 | Lovett |
| 6,364,278 | B1 | 4/2002 | Lin et al. |
| 6,391,985 | B1 | 5/2002 | Goode et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,895,280 | B2 | 5/2005 | Meadows et al. |
| 6,988,001 | B2 | 1/2006 | Greatbatch et al. |
| 6,993,384 | B2 | 1/2006 | Bradley et al. |
| 7,190,993 | B2 | 3/2007 | Sharma et al. |
| 7,244,150 | B1 | 7/2007 | Erase et al. |
| 7,288,108 | B2 | 10/2007 | DiMauro et al. |
| 7,395,118 | B2 | 7/2008 | Erickson |
| 7,437,193 | B2 | 10/2008 | Parramon et al. |
| 7,450,997 | B1 | 11/2008 | Pianca et al. |
| 7,672,734 | B2 | 3/2010 | Anderson et al. |
| 7,684,869 | B2 | 3/2010 | Bradley et al. |
| 7,736,382 | B2 | 6/2010 | Webb et al. |
| 7,761,165 | B1 | 7/2010 | He et al. |
| 7,783,359 | B2 | 8/2010 | Meadows |
| 7,792,590 | B1 | 9/2010 | Pianca et al. |
| 7,809,446 | B2 | 10/2010 | Meadows |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |
| 8,271,094 | B1 | 9/2012 | Moffitt et al. |
| 8,295,944 | B2 | 10/2012 | Howard et al. |
| 8,326,433 | B2 | 12/2012 | Blum et al. |
| 8,364,278 | B2 | 1/2013 | Pianca et al. |
| 8,391,985 | B2 | 3/2013 | McDonald |
| 8,463,343 | B2 | 6/2013 | Kuhn et al. |
| 8,473,061 | B2 | 6/2013 | Moffitt et al. |
| 8,483,237 | B2 | 7/2013 | Zimmermann et al. |
| 8,571,665 | B2 | 10/2013 | Moffitt et al. |
| 8,675,945 | B2 | 3/2014 | Barnhorst et al. |
| 8,688,235 | B1 | 4/2014 | Pianca et al. |
| 8,792,993 | B2 | 7/2014 | Pianca et al. |
| 8,831,731 | B2 | 9/2014 | Blum et al. |
| 8,831,742 | B2 | 9/2014 | Pianca et al. |
| 8,849,632 | B2 | 9/2014 | Sparks et al. |
| 8,936,630 | B2 | 1/2015 | Denison et al. |
| 8,958,615 | B2 | 2/2015 | Blum et al. |
| 9,415,154 | B2 | 8/2016 | Leven |
| 9,550,063 | B2 | 1/2017 | Wolf, II |
| 9,681,809 | B2 | 6/2017 | Sharma et al. |
| 9,931,511 | B2 * | 4/2018 | Kaula ................. G06F 3/04842 |
| 2002/0156513 | A1 | 10/2002 | Borkan |
| 2002/0161417 | A1 | 10/2002 | Scribner |
| 2004/0098063 | A1 * | 5/2004 | Goetz ................ A61N 1/36071 607/48 |
| 2004/0147964 | A1 * | 7/2004 | Nolan ................... A61N 1/325 607/3 |
| 2005/0216072 | A1 | 9/2005 | Mahadevan-Jansen et al. |
| 2006/0129210 | A1 | 6/2006 | Cantin et al. |
| 2006/0155348 | A1 | 7/2006 | deCharms |
| 2006/0161227 | A1 | 7/2006 | Walsh, Jr. et al. |
| 2007/0053996 | A1 | 3/2007 | Boyden et al. |
| 2007/0150036 | A1 | 6/2007 | Anderson |
| 2007/0161919 | A1 | 7/2007 | DiLorenzo |
| 2007/0244526 | A1 | 10/2007 | Zaghetto et al. |
| 2008/0046053 | A1 | 2/2008 | Wagner et al. |
| 2008/0077198 | A1 | 3/2008 | Webb et al. |
| 2008/0197300 | A1 | 8/2008 | Kayser et al. |
| 2009/0069871 | A1 | 3/2009 | Mahadevan-Jansen et al. |
| 2009/0118800 | A1 | 5/2009 | Deisseroth et al. |
| 2009/0187222 | A1 | 7/2009 | Barker |
| 2009/0196471 | A1 * | 8/2009 | Goetz ..................... G06T 7/73 382/128 |
| 2009/0276021 | A1 | 11/2009 | Meadows et al. |
| 2009/0287272 | A1 | 11/2009 | Kokones et al. |
| 2009/0287273 | A1 | 11/2009 | Carlton et al. |
| 2010/0076535 | A1 | 3/2010 | Pianca et al. |
| 2010/0114190 | A1 | 5/2010 | Bendett et al. |
| 2010/0174344 | A1 | 7/2010 | Dadd et al. |
| 2010/0268298 | A1 | 10/2010 | Moffitt et al. |
| 2010/0292758 | A1 | 11/2010 | Lee et al. |
| 2010/0324630 | A1 | 12/2010 | Lee et al. |
| 2011/0004267 | A1 | 1/2011 | Meadows |
| 2011/0005069 | A1 | 1/2011 | Pianca |
| 2011/0046432 | A1 | 2/2011 | Simon et al. |
| 2011/0078900 | A1 | 4/2011 | Pianca et al. |
| 2011/0112591 | A1 * | 5/2011 | Seymour ................ A61B 5/24 607/3 |
| 2011/0125077 | A1 | 5/2011 | Denison et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0172653 | A1 | 7/2011 | Schneider et al. |
| 2011/0172725 | A1 * | 7/2011 | Wells ................... A61N 5/0622 607/3 |
| 2011/0238129 | A1 | 9/2011 | Moffitt et al. |
| 2011/0295331 | A1 * | 12/2011 | Wells ................... A61N 1/0541 607/3 |
| 2011/0313500 | A1 | 12/2011 | Barker et al. |
| 2012/0014580 | A1 * | 1/2012 | Blum .................. A61N 1/36132 382/131 |
| 2012/0016378 | A1 | 1/2012 | Pianca et al. |
| 2012/0046710 | A1 | 2/2012 | Digiore et al. |
| 2012/0046715 | A1 | 2/2012 | Moffitt et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | Digiore et al. |
| 2012/0203321 | A1 | 8/2012 | Moffitt et al. |
| 2012/0253261 | A1 | 10/2012 | Poletto et al. |
| 2012/0265262 | A1 * | 10/2012 | Osorio ................. A61B 5/4094 607/3 |
| 2012/0265268 | A1 * | 10/2012 | Blum .................. A61N 1/36021 607/46 |
| 2012/0287420 | A1 | 11/2012 | McLaughlin et al. |
| 2012/0314924 | A1 | 12/2012 | Carlton et al. |
| 2012/0316615 | A1 | 12/2012 | Digiore et al. |
| 2013/0019325 | A1 | 1/2013 | Deisseroth et al. |
| 2013/0053905 | A1 | 2/2013 | Wagner |
| 2013/0102861 | A1 | 4/2013 | Oki et al. |
| 2013/0105071 | A1 | 5/2013 | Digiore et al. |
| 2013/0116744 | A1 | 5/2013 | Blum et al. |
| 2013/0197424 | A1 | 8/2013 | Bedenbaugh |
| 2013/0197602 | A1 | 8/2013 | Pianca et al. |
| 2013/0261684 | A1 | 10/2013 | Howard |
| 2013/0268026 | A1 | 10/2013 | Rao et al. |
| 2013/0304152 | A1 | 11/2013 | Bradley et al. |
| 2013/0317573 | A1 | 11/2013 | Zhu et al. |
| 2013/0317587 | A1 | 11/2013 | Barker |
| 2013/0325091 | A1 | 12/2013 | Pianca et al. |
| 2014/0039587 | A1 | 2/2014 | Romero |
| 2014/0067015 | A1 * | 3/2014 | Kothandaraman ................... A61N 1/37264 607/59 |
| 2014/0067023 | A1 | 3/2014 | Register et al. |
| 2014/0122379 | A1 | 5/2014 | Moffitt et al. |
| 2014/0142664 | A1 | 5/2014 | Roukes et al. |
| 2014/0163639 | A1 * | 6/2014 | Zhu ..................... A61N 1/0551 607/46 |
| 2014/0296953 | A1 | 10/2014 | Pianca et al. |
| 2014/0343647 | A1 | 11/2014 | Romero et al. |
| 2014/0353001 | A1 | 12/2014 | Romero et al. |

(56) References Cited

U.S. PATENT DOCUMENTS

| | | |
|---|---|---|
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0290461 A1* | 10/2015 | Min ............... A61N 1/36135 607/59 |
| 2015/0306414 A1 | 10/2015 | Nielsen et al. |
| 2015/0375006 A1 | 12/2015 | Denison et al. |
| 2016/0030749 A1 | 2/2016 | Carcieri et al. |
| 2016/0045740 A1* | 2/2016 | Rezai ............... A61N 1/36139 607/45 |
| 2016/0082251 A1* | 3/2016 | Moffitt ............... A61N 1/3616 607/46 |
| 2016/0082253 A1* | 3/2016 | Moffitt ............... A61N 1/36071 607/46 |
| 2016/0228692 A1 | 8/2016 | Steinke et al. |
| 2016/0271392 A1 | 9/2016 | Vallejo et al. |
| 2016/0271413 A1* | 9/2016 | Vallejo ............... A61N 1/36062 |
| 2016/0287885 A1 | 10/2016 | Saini |
| 2016/0346557 A1 | 12/2016 | Bokil |
| 2016/0375258 A1 | 12/2016 | Steinke |
| 2017/0061627 A1 | 3/2017 | Bokil |
| 2017/0136254 A1 | 5/2017 | Simon et al. |
| 2017/0225007 A1 | 8/2017 | Orinski |
| 2017/0259078 A1 | 9/2017 | Howard |
| 2017/0281966 A1 | 10/2017 | Basiony |
| 2017/0304633 A1 | 10/2017 | Zhang |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Carmona |
| 2018/0193655 A1 | 7/2018 | Zhang et al. |
| 2018/0229042 A1* | 8/2018 | Kaula ............... A61N 1/37247 |
| 2018/0256906 A1 | 9/2018 | Pivonka et al. |
| 2018/0369606 A1 | 12/2018 | Zhang et al. |
| 2018/0369607 A1 | 12/2018 | Zhang et al. |
| 2020/0094047 A1 | 3/2020 | Govea et al. |
| 2020/0155854 A1 | 5/2020 | Leven et al. |
| 2020/0376262 A1 | 12/2020 | Clark et al. |

FOREIGN PATENT DOCUMENTS

| | | |
|---|---|---|
| WO | 2011150430 | 12/2011 |
| WO | 2012/103543 | 8/2012 |
| WO | 2014/035731 | 3/2014 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |

OTHER PUBLICATIONS

Invitation to Pay Additional Fees for PCT Application No. PCT/US2019/012652 dated May 10, 2019.

Baxter, G.D. et al., Effects of Low Intensity Infrared Laser Irradiation Upon Conduction in the Human Median Nerve In Vivo, Experimental Physiology (1994) 79, 227-234.

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Tarnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

Brennan KC, Toga AW. Intraoperative Optical Imaging. In: Frostig RD, editor. In Vivo Optical Imaging of Brain unction. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemistry international.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

U.S. Appl. No. 16/242,370, filed Jan. 8, 2019, Zhang et al.

* cited by examiner

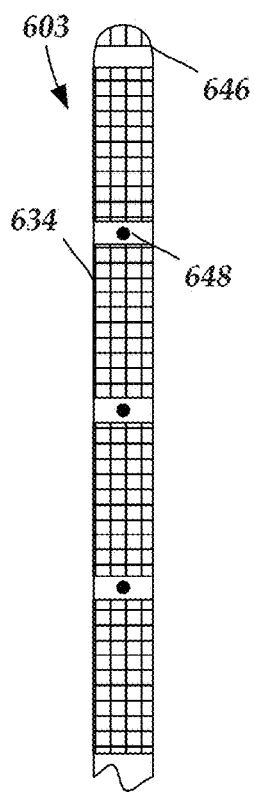 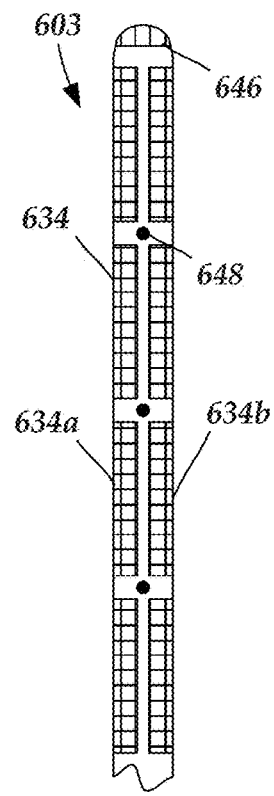 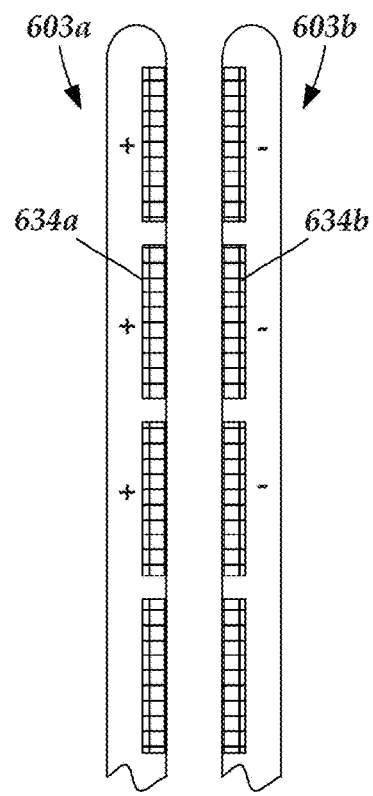
Fig. 6A          Fig. 6B          Fig. 6C
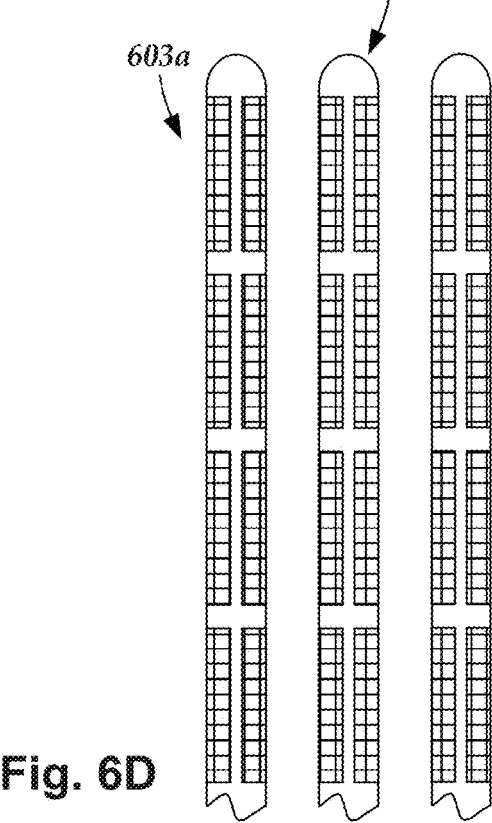 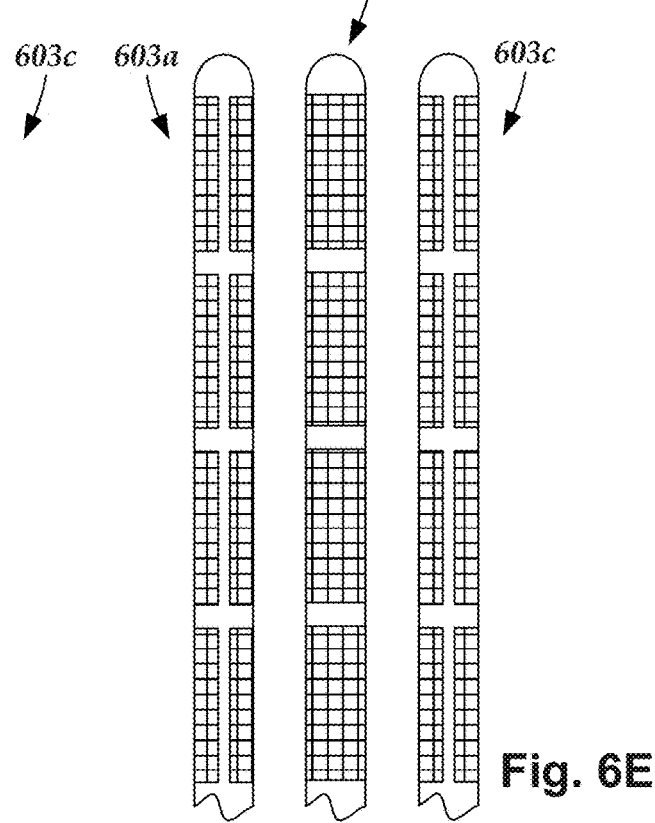
Fig. 6D                                    Fig. 6E

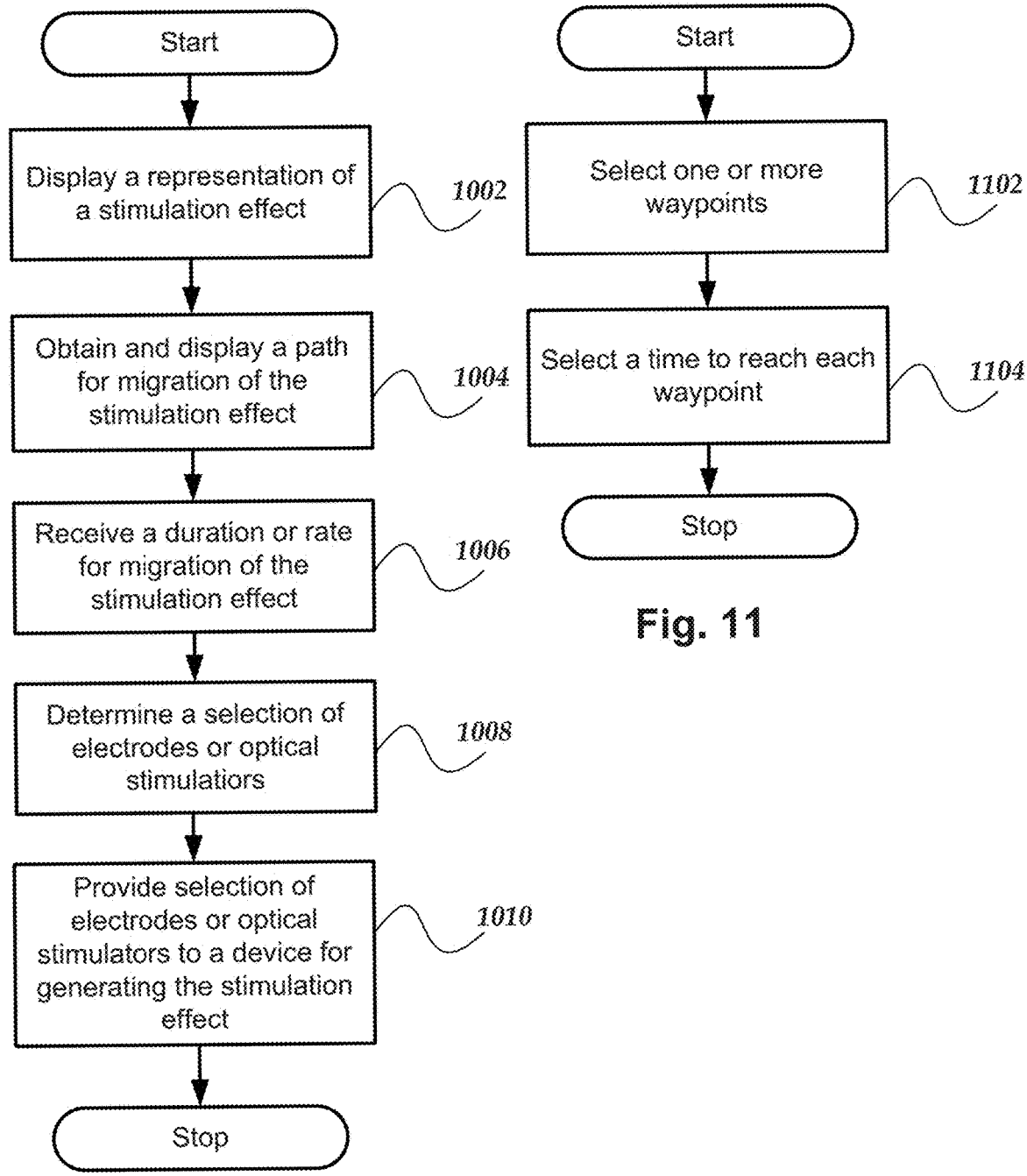

METHODS AND SYSTEMS FOR STIMULATION FOR GLIAL MODULATION

CROSS-REFERENCE TO RELATED APPLICATIONS

This application claims the benefit under 35 U.S.C. § 119(e) of U.S. Provisional Patent Application Ser. No. 62/616,360, filed Jan. 11, 2018, which is incorporated herein by reference.

FIELD

The present invention is directed to the area of implantable electrical stimulation systems and methods of making and using the systems. The present invention is also directed to methods and systems for glial stimulation including stimulation of glial cells in the spinal cord.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a system for planning or conducting stimulation. The system includes displaying, on the display, a representation of a stimulation effect; obtaining and displaying, on the display, a path for migration of the stimulation effect; receiving a duration or rate for migration of the stimulation effect along the path; and determining a selection of one or more electrodes or optical stimulators for one or more stimulation leads of a stimulation system to produce the stimulation effect and conduct the migration of the stimulation effect along the path according to the duration or rate.

Another embodiment is a method for planning or conducting stimulation. The method includes displaying, on the display, a representation of a stimulation effect; obtaining and displaying, on the display, a path for migration of the stimulation effect; receiving a duration or rate for migration of the stimulation effect along the path; and determining a selection of one or more electrodes or optical stimulators for one or more stimulation leads of a stimulation system to produce the stimulation effect and conduct the migration of the stimulation effect along the path according to the duration or rate.

Yet another embodiment is non-transitory processor readable storage media that includes instructions for planning or conducting stimulation, wherein execution of the instructions by one or more processor devices performs actions, including: displaying, on the display, a representation of a stimulation effect; obtaining and displaying, on the display, a path for migration of the stimulation effect; receiving a duration or rate for migration of the stimulation effect along the path; and determining a selection of one or more electrodes or optical stimulators for one or more stimulation leads of a stimulation system to produce the stimulation effect and conduct the migration of the stimulation effect along the path according to the duration or rate.

In at least some embodiments of the preceding system, method, and media, the stimulation effect comprises an effect associated with an electrical stimulation field. In at least some embodiments of the preceding system, method, and media, the stimulation effect comprises an effect associated with an optical stimulation field. In at least some embodiments of the preceding system, method, and media, the stimulation effect comprises an effect associated with an electrical stimulation field and an optical stimulation field.

In at least some embodiments of the preceding system, method, and media, the instructions are further configured for or the steps further include initiating a signal to deliver the selection of the one or more electrodes or optical stimulators to a stimulation system to generate the stimulation effect for delivery to a patient.

In at least some embodiments of the preceding system, method, and media, the instructions are further configured for or the steps further include receiving an indication of whether to repeat migration of the stimulation effect along the path (for example, in the same direction along the path or in the reverse direction along the path). In at least some embodiments of the preceding system, method, and media, the instructions are further configured for or the steps further include receiving a plurality of waypoints along the path. In at least some embodiments of the preceding system, method, and media, the instructions are further configured for or the steps further include receiving a time for each of the plurality of waypoints. In at least some embodiments of the preceding system, method, and media, the instructions are further configured for or the steps further include receiving a stimulation target, wherein the stimulation target is a type of cell (for example, neuron or glial cell).

In at least some embodiments of the preceding system, method, and media, the instructions are further configured for or the steps further include receiving a type of stimulation effect. In at least some embodiments of the preceding system, method, and media, the instructions are further configured for or the steps further include receiving a size change parameter describing a change in a size of the stimulation effect as the stimulation effect migrates along the path. In at least some embodiments of the preceding system, method, and media, the stimulation effect is configured for stimulation of glial cells, wherein the instructions are further configured for or the steps further include displaying, on the display, a representation of a neuronal stimulation field.

In at least some embodiments of the preceding system, method, and media, the instructions are further configured for or the steps further include displaying, on the display, a representation of another stimulation field. In at least some embodiments of the preceding system, method, and media, the instructions are further configured for or the steps further include receiving an indication regarding acceptability of overlap between the other stimulation field and the stimulation effect during migration of the stimulation effect along the path. In at least some embodiments of the preceding system, method, and media, the instructions are further configured for or the steps further include modifying the path to reduce or avoid the overlap between the other stimulation field end the stimulation effect.

Yet another embodiment is a system for programming a stimulation device. The system includes a display; and a computing device coupled to the display, wherein the computing device is configured for presenting a user interface on the display. The user interface includes a field representation of a stimulation effect; a target selection control configured to receive input of a target type of cell; an effect selection control configured to receive input of a type of stimulation effect; and a path control configured to receive input of a path for migration of the stimulation effect.

A further embodiment is a non-transitory processor readable storage media that includes instructions for presenting a user interface. The user interface includes a field representation of a stimulation effect; a target selection control configured to receive input of a target type of cell; an effect selection control configured to receive input of a type of stimulation effect; and a path control configured to receive input of a path for migration of the stimulation effect.

Another embodiment is a method of planning or conducting stimulation. The method includes presenting a user interface. The user interface includes a field representation of a stimulation effect; a target selection control configured to receive input of a target type of cell; an effect selection control configured to receive input of a type of stimulation effect; and a path control configured to receive input of a path for migration of the stimulation effect.

In at least some embodiments of the preceding system, method, and media, the user interface further includes a waypoint control configured to receive input of one or more waypoints along the path. In at least some embodiments of the preceding system, method, and media, the user interface further includes a waypoint time control configured to receive input of a time or rate at which the waypoint is to be reached. In at least some embodiments of the preceding system, method, and media, the user interface further includes a cycling control configured to select whether the path is repeated in a same direction or a reverse direction.

In at least some embodiments of the preceding system, method, and media, the user interface further includes a duration control for selecting a duration of the migration of the stimulation effect along the path. In at least some embodiments of the preceding system, method, and media, the user interface further includes an anatomical representation of a portion of anatomy. In at least some embodiments of the preceding system, method, and media, the user interface further includes a lead representation of at least one stimulation lead configured for electrical stimulation, optical stimulation, or both.

In at least some embodiments of the preceding system, the system further comprises a stimulation device and one or more stimulation leads, wherein the processor is configured for initiating a signal to deliver a selection of the one or more electrodes or optical stimulators to the stimulation device to generate the stimulation effect for delivery to a patient through the one or more stimulation leads. In at least some embodiments of the preceding method and media, the instructions are further configured for or the steps further include initiating a signal to deliver a selection of the one or more electrodes or optical stimulators to a stimulation system to generate the stimulation effect for delivery to a patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 6A is a schematic, side view of one embodiment of a portion of a percutaneous lead including at least one non-electrical sensor or optical stimulator, according to the invention;

FIG. 6B is a schematic, side view of another embodiment of a portion of a percutaneous lead including at least one non-electrical sensor or optical stimulator, according to the invention;

FIG. 6C is a schematic, side view of one embodiment of an arrangement of percutaneous leads, according to the invention;

FIG. 6D is a schematic, side view of another embodiment of an arrangement of percutaneous leads, according to the invention;

FIG. 6E is a schematic, side view of a third embodiment of an arrangement of percutaneous leads, according to the invention;

FIG. 10 is a flowchart of one embodiment of a method for planning or conducting stimulation, according to the invention;

FIG. 11 is a flowchart of one embodiment of a method for defining a path for migration of a stimulation effect, according to the invention;

DETAILED DESCRIPTION

The present invention is directed to the area of implantable electrical stimulation systems and methods of making and using the systems. The present invention is also directed to methods and systems for glial stimulation including stimulation of glial cells in the spinal cord.

The present patent application incorporates by reference, in its entirety, U.S. Provisional Patent Application No. 62/616,362 entitled "Implantable Stimulation Leads for Glial Modulation and Methods of Making and Using Same", filed on Jan. 11, 2018.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; 6,391,985; 8,473,061; 8,571,665; and 8,792,993; and U.S. Patent Applications Publication Nos. 2007/0150036; 2009/0187222; 2009/0276021; 2010/0076535; 2010/0268298; 2011/0004267; 2011/0005069; 2011/0078900; 2011/0130816; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2013/0197424; 2013/0197602; 2014/0039587; 2014/0353001; 2014/0358207; 2014/0358208; 2014/0358209; 2014/0358210; 2015/0018915; 2015/0045864; 2015/0051681; 2015/0066120; 2015/0151113; and 2016/0228692, all of which are incorporated by reference in their entireties.

Figure 1:
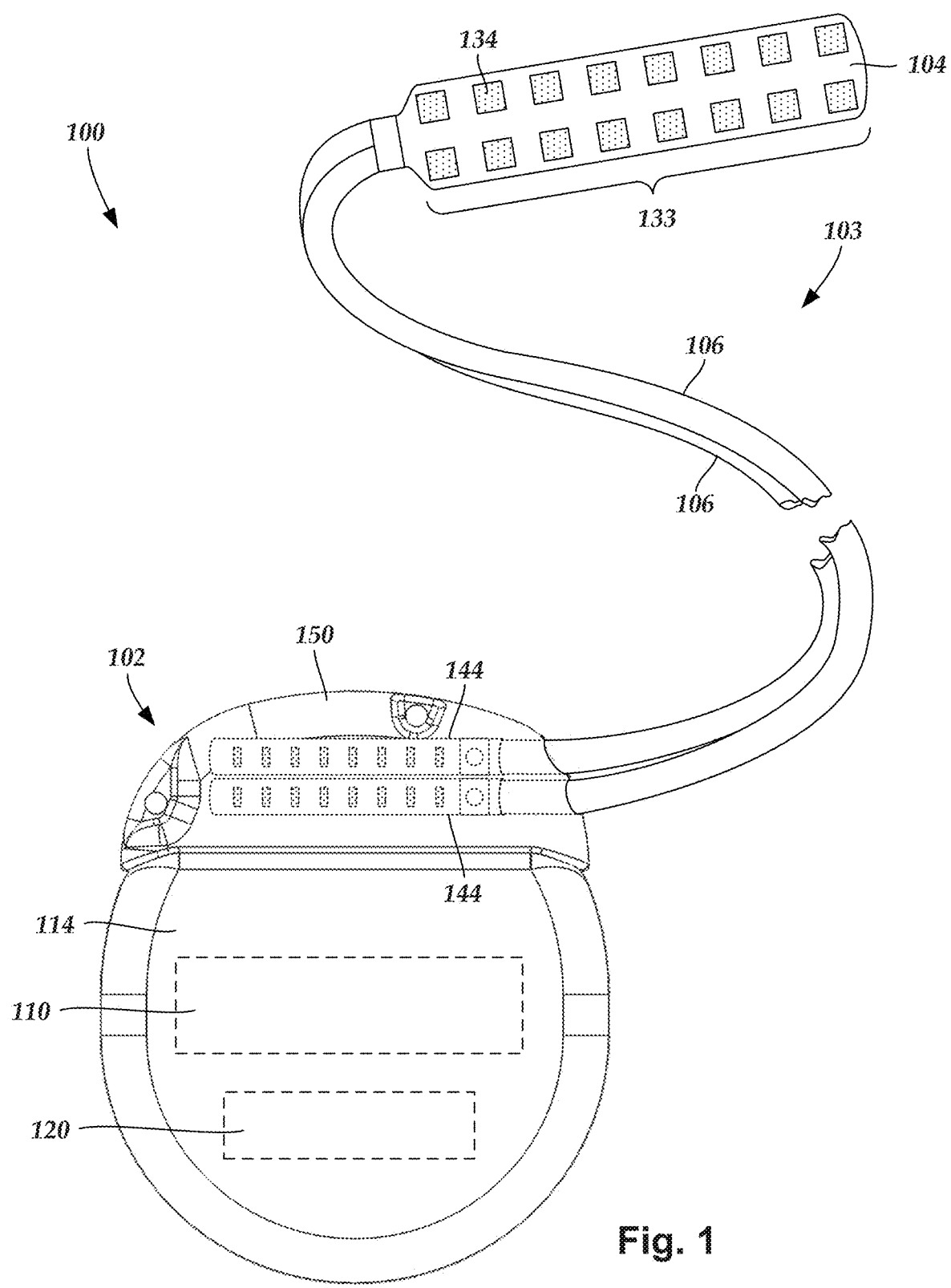
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 includes a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
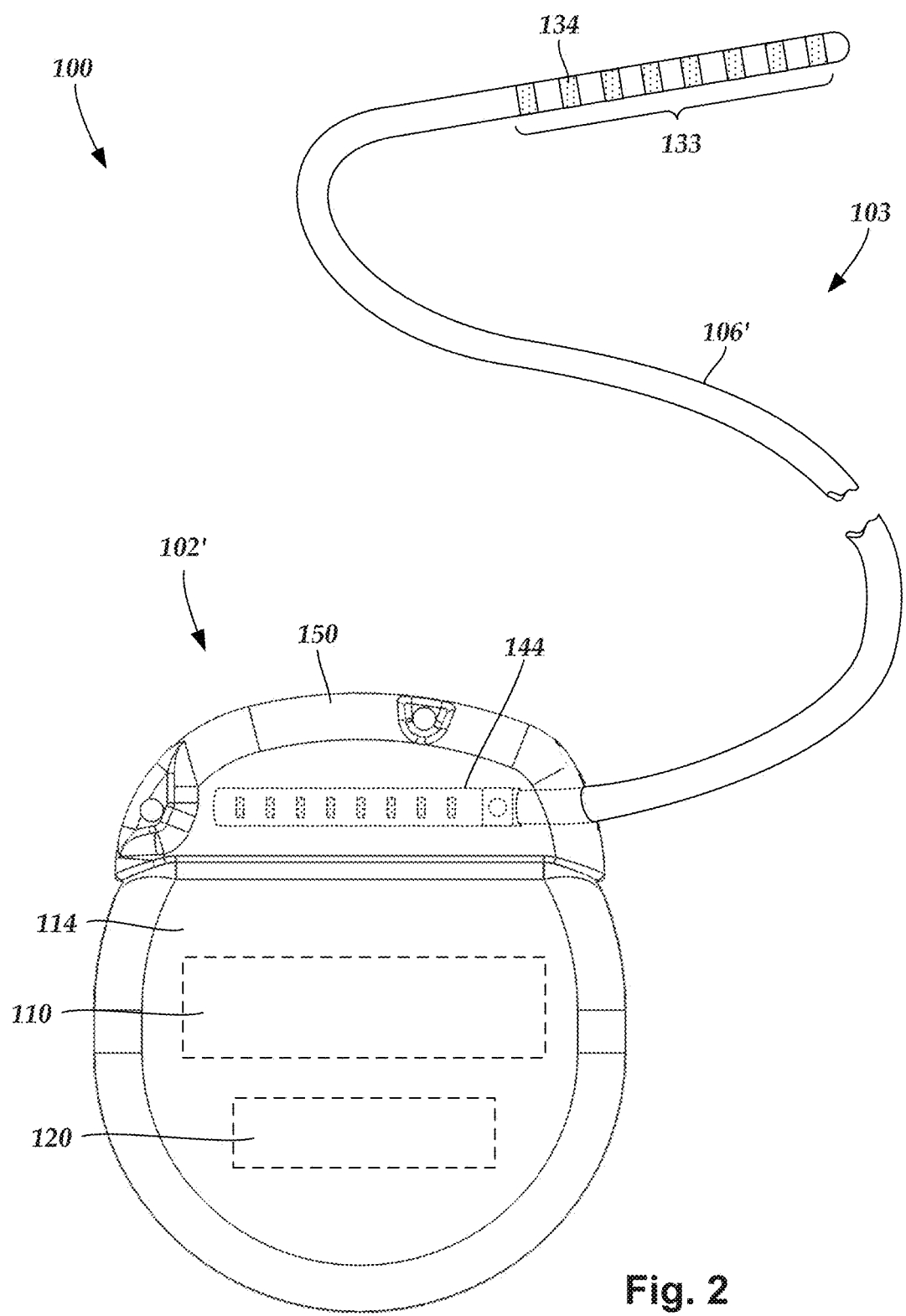
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, glial modulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
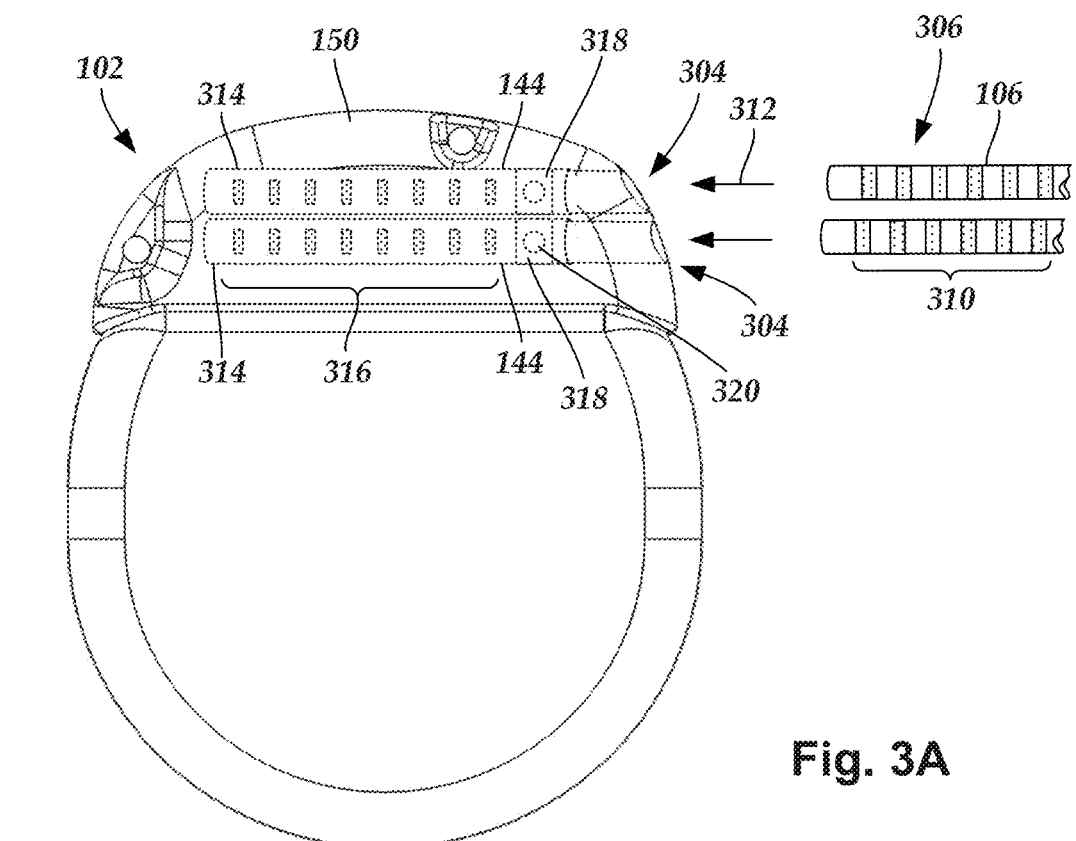
FIG. 3A is a schematic view of one embodiment of a plurality of connector assemblies disposed in the control module of FIG. 1, the connector assemblies configured to receive the proximal portions of the lead bodies of FIG. 1, according to the invention.
Figure 3B:
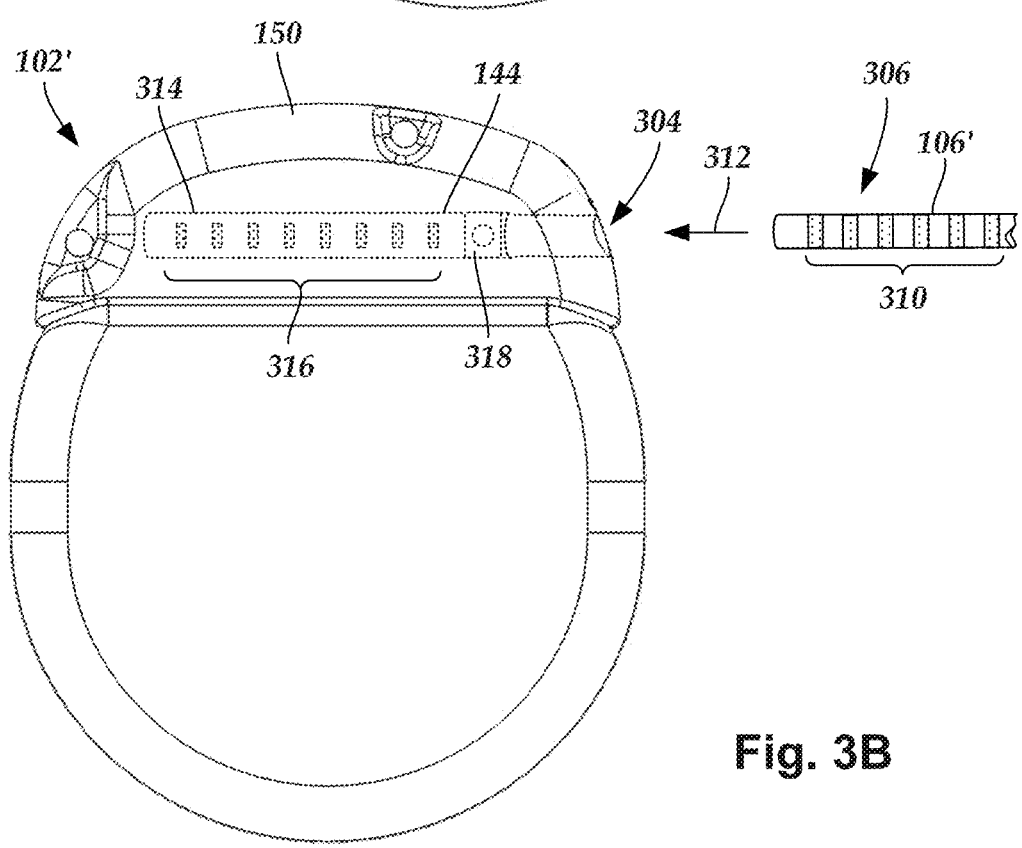
FIG. 3B is a schematic view of one embodiment of a connector assembly disposed in the control module of FIG. 2, the connector assembly configured to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured for insertion to the control module 102. FIG. 3B is a schematic side view of one embodiment of a single connector assembly 144 disposed on the control module 102'. In FIG. 3B, the proximal end 306 of the single lead body 106' is shown configured for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference in their entireties.

Figure 3C:
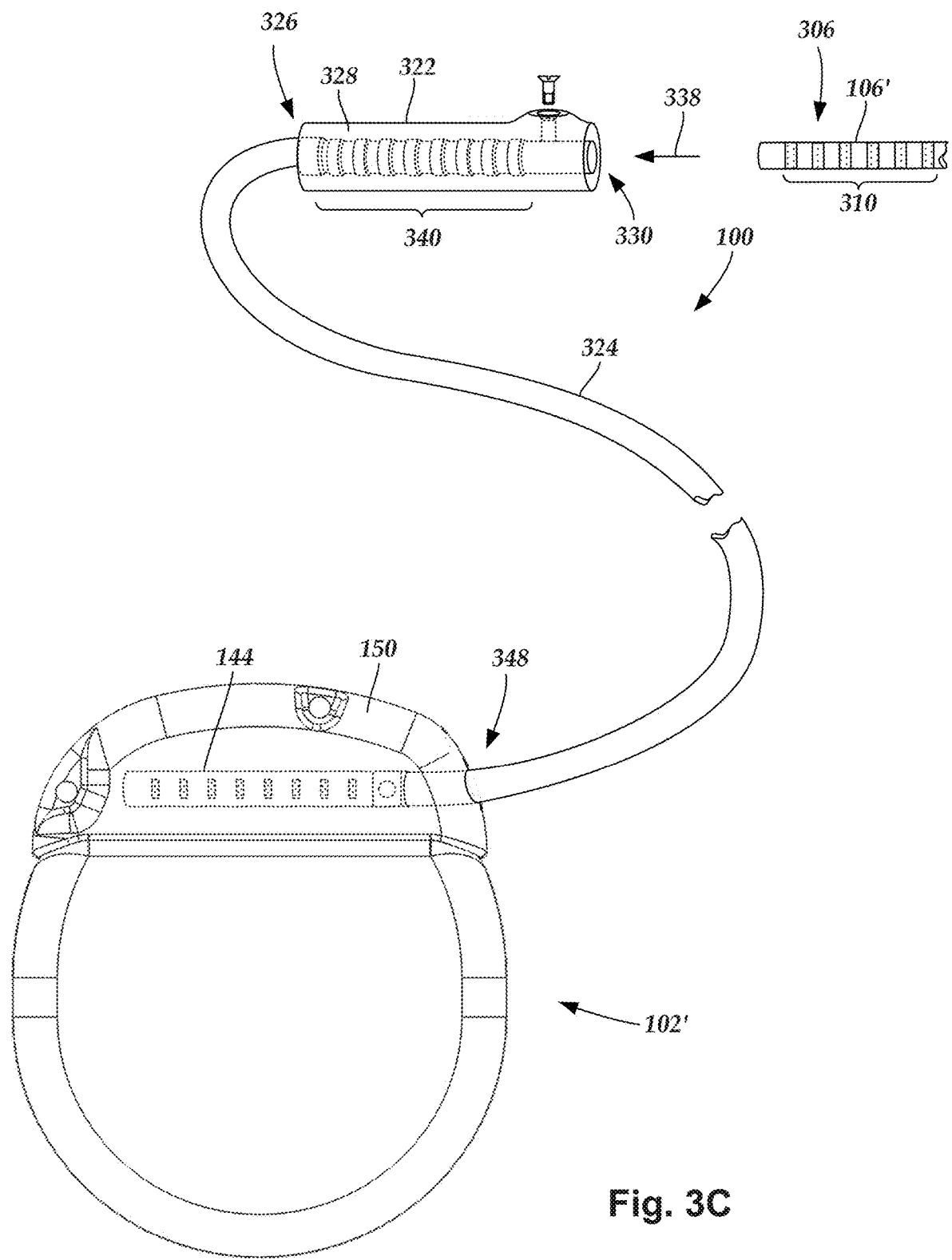
FIG. 3C is a schematic view of one embodiment of a proximal portion of the lead body of FIG. 2, a lead extension, and the control module of FIG. 2, the lead extension configured to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured for insertion into a lead extension connector assembly disposed in another lead extension. In other embodiments (as shown in FIG. 3C), the proximal end 348 of the lead extension 324 is configured for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Stimulation of patient tissue, such as the spinal cord, can be useful in reducing pain and providing other therapy. There is an increasing interest in the role of glial cells in chronic pain. Conventional spinal cord stimulation, however, is generally focused solely on modulating neuronal cells. Electrode configurations and stimulation patterns, including migratory stimulation, can be used to target glial cells, such as microglia, astrocytes, or oligodendrocytes or the like or any combination thereof, to promote healing, reduce inflammation, or relieve pain (or any combination thereof) In at least some embodiments, mechanisms such as, for example, electrotaxis, chemotaxis, galvanotaxis, or electromechanical effects produced by Lorenz interactions caused by an applied waveform (or any combination thereof) can be utilized to modulate glial cells.

In at least some embodiments, the glial cells that are to be stimulated reside in the dorsal horns. In contrast, conventional paddle leads for spinal cord stimulation typically have electrodes arranged to stimulate the neurons in the spinal columns.

Figure 4:
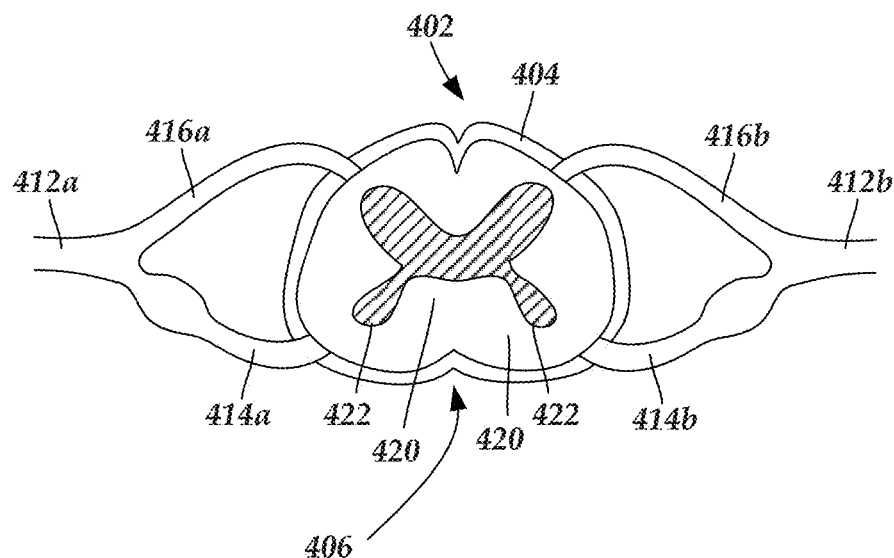
FIG. 4 is a schematic cross-sectional view of a portion of the spinal cord.

FIG. 4 schematically illustrates a transverse cross-sectional view of a spinal cord 402 surrounded by dura 404. The spinal cord 402 includes the dorsal (or posterior) column 420 and the dorsal (or posterior) horns 422. The spinal cord 402 also includes a midline 406 and multiple levels from which spinal nerves 412a and 412b extend. In FIG. 4, the spinal nerves 412a and 412b are shown attaching to the spinal cord 402 at a particular spinal cord level via corresponding dorsal roots 414a and 414b and ventral (or anterior) roots 416a and 416b. Typically, the dorsal roots 414a and 414b relay sensory information into the spinal cord 402 and the ventral roots 416a and 416b relay motor information outward from the spinal cord 402.

It will be understood that the leads, systems, and methods described herein are not dependent on any particular biological theory or theory of operation or effect. Moreover, the leads, systems, or methods should not be understood, interpreted, or viewed in relation to any particular biological theory or theory of operation or effect, unless indicated otherwise.

It is thought that in chronic pain states microglia may assume an activated hypertrophic phenotype, may proliferate, and may contribute to the maintenance of chronic pain. Nerve injury may activate microglia in the dorsal horn of the spinal cord. It has been suggested that the resultant hyperexcitability in the dorsal horn pain network induced by factors from activated microglia may be at least partially responsible for neuropathic pain. Moreover, it is thought possible that activated glial cells, astrocytes and microglia within the spinal cord could maintain the pain sensation even after the original injury or inflammation has healed, and convert it into chronic by altering neuronal excitability.

It is also found that microglia can be highly motile cells that may migrate hundreds of micrometers toward damaged or infected sites as a response to a number of chemical species, such as, for example, ATP/ADP or lysophosphatidic acid. It has been suggested that microglia respond to extracellular ATP by releasing ATP to provide a positive feedback mechanism to generate a long-range extracellular signal for attracting distant microglia to migrate towards and accumulate at the site of an injury.

It has been suggested that pain-related glial cells in the spinal cord are often largely isolated to the dorsal horns. Conventional paddle leads are typically arranged with electrodes for dorsal column stimulation. In contrast, in at least some embodiments, a paddle lead for glial cell stimulation can include electrodes spaced further apart mediolaterally in order to be positioned over or near the dorsal horns. In some embodiments, a paddle lead may include one or multiple columns for one or both of the lateral aspects and, optionally, a medial sensor array or an array of non-electrode stimulators or any combination thereof.

In at least some embodiments, the electrodes may also be longer in the longitudinal direction than electrodes used for neuronal stimulation. It is believed that shorter electrodes are more likely to stimulate neurons which are activated by variations in the electric field (for example, variations indicated by the second difference of the electric field). In contrast, in at least some embodiments, longer electrodes can produce an electrical field effect to facilitate cytotaxis of glial cells, optionally without (or with reduced) neuronal stimulation.

The term "stimulation effect" includes, but is not limited to, an electric field, an electric field effect, an electrical stimulation field (or effect thereof), an optical field (or effect thereof), or an optical stimulation field (or an effect thereof), or any combination thereof. A stimulation effect may also produce effects other than neuronal or cellular stimulation including, but not limited to, cytotaxis, electrotaxis, galvanotaxis, chemotaxis, Lorentz forces that may modulate the release of gliomodulators, or the like.

In the description below, an electrical field effect is used as an example, but the electrical field effect can be replaced by any other stimulation field effect that produces a desired result. In the description below, an electrical stimulation system which uses electrodes is used as an example, but the electrical stimulation system can be replaced by, for example, an optical stimulation system with optical stimulators (instead of electrodes) or a combined electrical/optical stimulation system. It will be recognized, however, that electrical stimulation and optical stimulation are not necessarily interchangeable to produce a desired effect. Electrical stimulation and optical stimulation can interact with cells and other body tissues in very different ways and can produce different effects.

Figure 5:
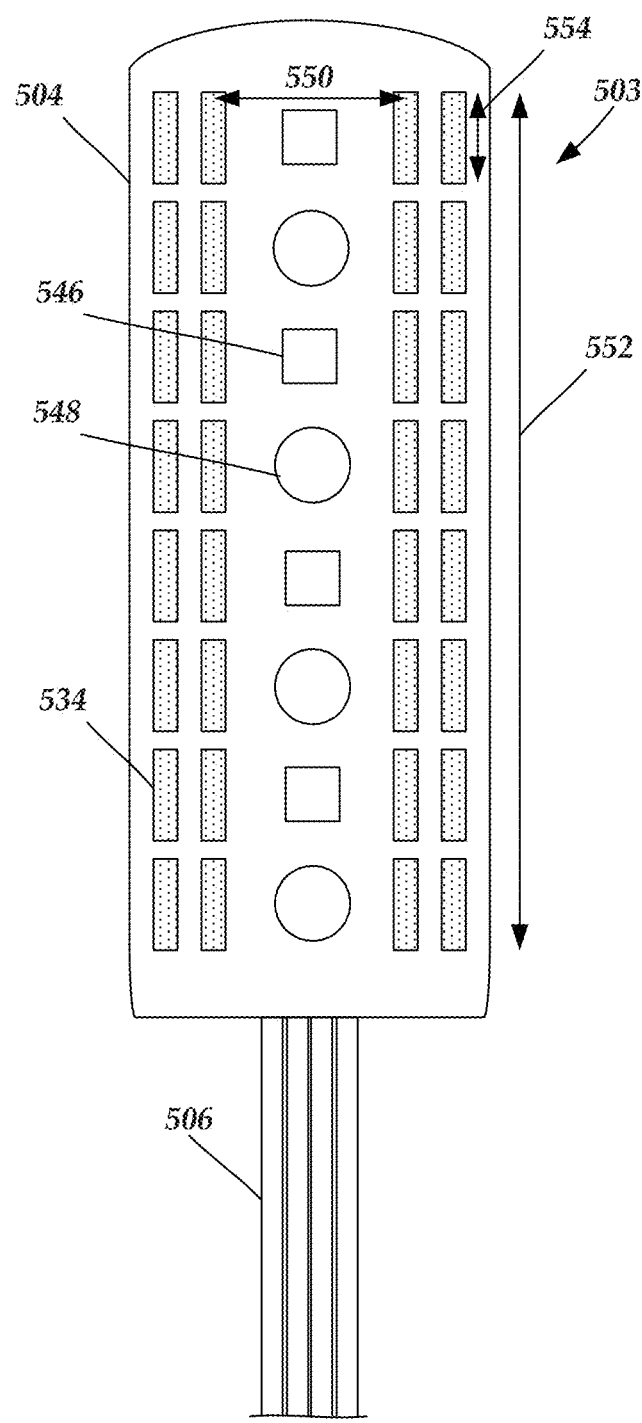
FIG. 5 is a schematic, side view of one embodiment of a portion of a paddle lead with spaced apart columns of electrodes for glial modulation, according to the invention.

FIG. 5 illustrates one embodiment of a paddle lead 503 with a paddle body 404, multiple columns of electrodes 534, and one or more lead bodies 506 extending from the paddle body 504. The illustrated embodiment also includes one or more optional sensors 546 and one or more optional optical stimulators 548.

The paddles lead 503 includes multiple columns of electrodes 534 along the paddle body 504 with the columns spaced further apart laterally than electrodes used for dorsal column stimulation because the dorsal horns are outside the dorsal column. For example, to stimulate the dorsal horn the columns of electrodes can be spaced apart laterally by a distance 550 of, for example, 7 to 12 mm (center-to-center) or more. This distance may vary depending on the position in the spinal cord where the paddle lead is intended for implantation. Many conventional paddle leads have a total lateral width of no more than 8 mm or less and, therefore, center-to-center lateral spacing between two columns of electrodes for such leads is typically in the range of 6 mm or less.

In the illustrated embodiment, the paddle lead 503 has two columns of electrodes 534 on each lateral side. It will be understood that in other embodiments, there may be one, three, four, or more columns on each side and that the number of columns on each lateral side may be the same or different. In addition, the electrodes 534 in the columns may be aligned with each other, as illustrated in FIG. 5, or may be staggered relative to each other. In at least some embodiments, the columns of electrodes 534 are selected to be relatively long when compared to the electrodes of conventional paddle leads to facilitate cytotaxis of glial cells along a migratory path defined by spatial and temporal variation of the stimulation along the length of the paddle lead. For example, the length 552 of the column of electrodes 534 can be at least 120, 125, 130, 132, 135, 140, 145, or 150 mm or more.

Each of the columns can include any number of electrodes 534 including, but not limited to, one, two, three, four, five, six, seven, eight, nine, ten, twelve, sixteen, or more electrodes. The electrodes 534 in each of the columns can be spaced apart longitudinally in a uniform manner, as illustrated in FIG. 5, or in any other regular or irregular pattern. The electrodes 534 can be identical in size and shape or differ in size or shape. The columns may have the same number of electrodes 534a or different numbers of electrodes. The columns can be identical with respect to arrangement of the electrodes 534a or can be different. In at least some embodiments, one or more (or all) of the electrodes 534 are selected to be relatively long when compared to electrodes of conventional paddle leads to facilitate stimulation of glial cells with reduced or no stimulation of neuronal cells. For example, the length 554 of the electrode 534 can be at least 4, 5, 6, 7, or 8 mm or more. In at least some embodiments, the longitudinal spacing between electrodes in a column is at least 0.5 mm.

The optional sensors 546 can be any suitable type of sensor including, but not limited to, optical sensors, piezoelectric sensors, chemical sensors, accelerometers, or the like. The paddle lead may include one, two, three, four, or more sensors. The sensors may be identical or may be different (for example, different types of sensors or sensors for different types of chemicals or signals). In at least some embodiments, a sensor 546 is connected to one or more terminals (for example, terminals 310 of FIG. 3A or 3B or additional terminals) at the proximal end of the lead via one or more conductors. Alternatively or additionally, a sensor 546 can be wirelessly coupled to a control module, programming unit (see, FIG. 7), or any other suitable device using Bluetooth™, rf transmission, or any other suitable transmission arrangement.

The optional optical stimulators 548 can be any suitable type of optical stimulator including, but not limited to, light emitting diodes (LEDs), organic light emitting diodes (OLEDs), or the terminal end of an optical fiber that is coupled, or coupleable, to a light source in the paddle lead or control module or other device. The paddle lead may include one, two, three, four, or more optical stimulators. The optical stimulators may be identical or may be different (for example, emit different wavelengths of light). A paddle lead may include one or more sensors or one or more optical stimulators or any combination thereof. In at least some embodiments, an optical stimulator 548 is connected to one or more terminals (for example, terminals 310 of FIG. 3A or 3B or additional terminals) at the proximal end of the lead via one or more conductors. If the optical stimulator is an optical fiber, the optical fiber may be coupled to an optical terminal at the proximal end of the lead (for example, when the light source is external to the lead such as located in the control module or other device) or to a light source, such as a light emitting diodes (LEDs), organic light emitting diodes (OLEDs), or the like within the lead.

In some embodiments, the paddle lead 503 can include additional medial electrodes (not shown) for stimulation or for sensing. These additional electrodes can be formed as one or more columns and may be the same size as the electrodes 534 or may be sized differently (for example, to stimulate neuronal tissue by being smaller in longitudinal length).

Percutaneous or isodiametric leads can be used instead of, or in addition to, paddle leads. One or more percutaneous leads can be implanted for spinal cord stimulation. For example, one or more percutaneous leads can be implanted on each lateral side of the spinal cord and arranged over or near the dorsal horns. Optionally, a medial lead may also be implanted.

FIG. 6A illustrates one embodiment of a percutaneous lead 603 with multiple electrodes 634, one or more optional sensors 646, and one or more optional optical stimulators 648. In the embodiment of FIG. 6A, the electrodes 634 are cylindrical. In at least some embodiments, the set of electrodes 634 are selected to be relatively long when compared to the electrodes of conventional percutaneous leads to facilitate cytotaxis of glial cells along a migratory path defined by spatial and temporal variation of the stimulation along the length of the paddle lead. For example, the length from the distal-most electrode to the proximal-most electrode can be at least 120, 125, 130, 132, 135, 140, 145, or 150 mm or more.

The lead 603 can include any number of electrodes 634 including, but not limited to, one, two, three, four, five, six, seven, eight, nine, ten, twelve, sixteen, or more electrodes. The electrodes 634 can be spaced apart longitudinally in a uniform manner, as illustrated in FIG. 6, or in any other regular or irregular pattern. The electrodes 634 can be identical in size and shape or differ in size or shape. In at least some embodiments, one or more (or all) of the electrodes 634 are selected to be relatively long when compared to electrodes of conventional percutaneous leads to facilitate stimulation of glial cells with reduced or no stimulation of neuronal cells. For example, the length of the electrode 634 can be at least 4, 5, 6, 7, or 8 mm or more. In at least some embodiments, the longitudinal spacing between electrodes is at least 0.5 mm.

The optional sensors 646 and optional optical stimulators 648 can be any of those described above with respect to the embodiment illustrated in FIG. 5. Moreover, the optional sensors 646 and optional optical stimulators 648 can be positioned at the tip of the lead, between electrodes, or proximal to all of the electrodes, or any combination thereof and are not limited to the positions illustrated in FIG. 6. A percutaneous lead may include one or more sensors or one or more optical stimulators or any combination thereof. In at least some embodiments, a sensor 646 is connected to one or more terminals (for example, terminals 310 of FIG. 3A or 3B or additional terminals) at the proximal end of the lead via one or more conductors. Alternatively or additionally, a sensor 646 can be wirelessly coupled to a control module, programming unit (see, FIG. 7), or any other suitable device using Bluetooth™, rf transmission, or any other suitable transmission arrangement. In at least some embodiments, an optical stimulator 648 is connected to one or more terminals (for example, terminals 310 of FIG. 3A or 3B or additional terminals) at the proximal end of the lead via one or more conductors. If the optical stimulator is an optical fiber, the optical fiber may be coupled to an optical terminal at the proximal end of the lead (for example, when the light source is external to the lead such as located in the control module or other device) or to a light source, such as a light emitting diodes (LEDs), organic light emitting diodes (OLEDs), or the like within the lead.

FIG. 6B illustrates another embodiment of a percutaneous lead 603 with multiple electrodes 634, one or more optional sensors 646, and one or more optional optical stimulators 648. In the embodiment of FIG. 6, the electrodes 634 are segmented electrodes and do not extend around the entire circumference of the lead. In the illustrated embodiment of FIG. 6B, there is a set of two segmented electrodes 634a, 634b at each longitudinal position along the lead. Each of these segmented electrodes 634a, 634b extends no more than 160, 150, 145, 140, 135, 100, or 90 degrees around the circumference of the lead 603. In other embodiments, there may be three, four, or more electrodes in each set. In at least some embodiments, each set of electrodes includes the same number of segmented electrodes. Alternatively, the sets of electrodes may include different numbers of segmented electrodes.

Segmented electrodes may provide for superior current steering than cylindrical or ring electrodes because target structures in electrical stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to 1 target tissue, while potentially avoiding stimulation of other tissue. Examples of leads with segmented electrodes include U.S. Pat. Nos. 8,473,061; 8,571,665; and 8,792,993; and U.S. Patent Application Publications Nos. 2010/0268298; 2011/0130803; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358207; 2014/0358208; 2014/0358209; 2014/0358210; 2015/0045864; 2015/0066120; 2015/0018915; 2015/0051681; 2015/0151113; and 2016/0228692, all of which are incorporated herein by reference in their entireties.

In some embodiments, a lead may include a combination of segmented electrodes (FIG. 6B) and cylindrical or ring electrodes (FIG. 6A). Any suitable combination and arrangement of these types of electrodes can be used. The arrangement, length of the array of electrodes, length of individual electrodes, and longitudinal spacing between the electrodes an embodiment with segmented electrodes can be the same as described above for the embodiment illustrated in FIG. 6A.

FIG. 6C illustrates an arrangement of two percutaneous leads 603a, 603b with segmented electrodes 634a, 634b that are implanted adjacent to each other. For example, the lead 603a can be implanted over the dorsal horn in a lateral position and the lead 603b can be implanted medially with respect to the spinal cord. Alternatively, the two leads 603a, 603b can be implanted laterally with respect to the spinal cord (for example, over or near the two dorsal horns.)

This arrangement can be particularly useful for generating mediolateral bipolar fields by selecting one or more of the electrodes on one lead as anodes and one or more electrodes of the other lead as cathodes. One example of such an arrangement is indicated by the distribution of "+" and "−" signs in FIG. 6C. By using multiple electrodes of each lead, a broad region with an electrical field effect in a medial aspect can be generated to facilitate cytotaxis of glial cells. Of course, a similar arrangement can be made using the leads of either FIG. 6A or 6B (or a combination of these two leads).

FIGS. 6D and 6E illustrate two arrangements of three percutaneous leads 603a, 603b, 603c. For example, the leads 603a, 603c can be implanted laterally with respect to the spinal cord (for example, over or near the two dorsal horns) and the lead 603b can be implanted medially. These arrangements may provide for further control to produce mediolateral fields or produce fields that can be used to migrate or steer glial cells or glial functionality along the regions of the spinal cord covered by the leads.

In at least some embodiments, the lead can be designed for intradural placement. In at least some embodiments, the lead may include a drug eluting lumen or drug-delivering surface, for example, to promote gliomodulatory effects, such as chemotaxis, in response to drug elution or to produce pro- or anti-inflammatory effects or any combination thereof.

Alternatively, or in addition, to stimulation of the dorsal horn region, one or leads (percutaneous or paddle leads) may be provided for stimulation of the dorsal columns, dorsal column nuclei and caudal medulla (with cervical implant), dorsal roots, spinocerebellar (dorsolateral) tracts, for example, for proprioception, dorsal root ganglia (DRG) or satellite ganglion cells, dorsolateral funiculus, peripheral nerves and Schwann cells, ventral horns, ventral roots, ventrolateral tracts (e.g. anterolateral STT, for example, for pain modulation), ventromedial tracts (rubrospinal, medullary pyramidal tract) for example, for motor control and modulation, or any combination thereof. In some embodiments, stimulation for multiple regions may be provided by the same lead. In some embodiments, stimulation of different regions may be provided using different leads.

Figure 7:
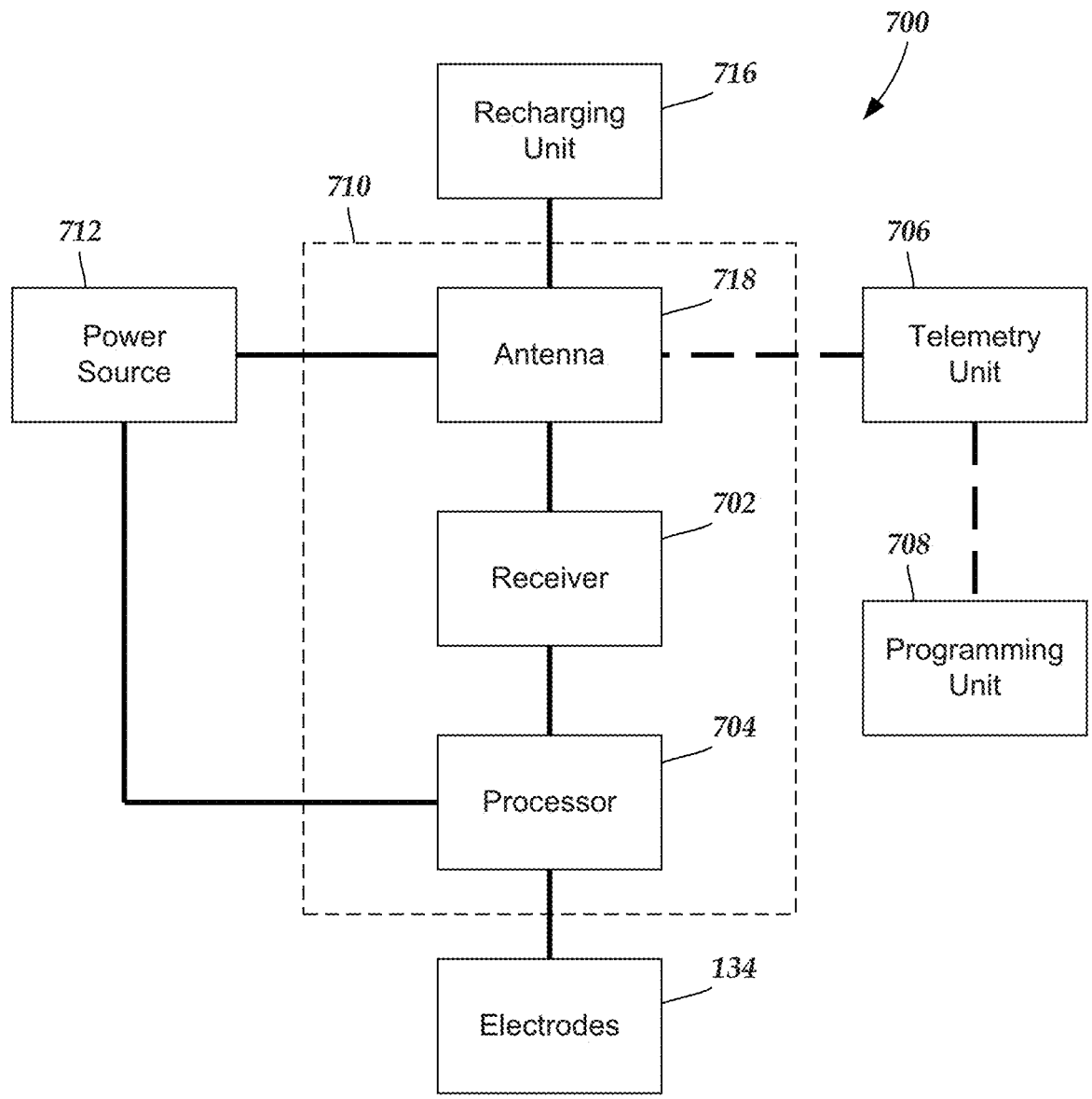
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

Figure 8:
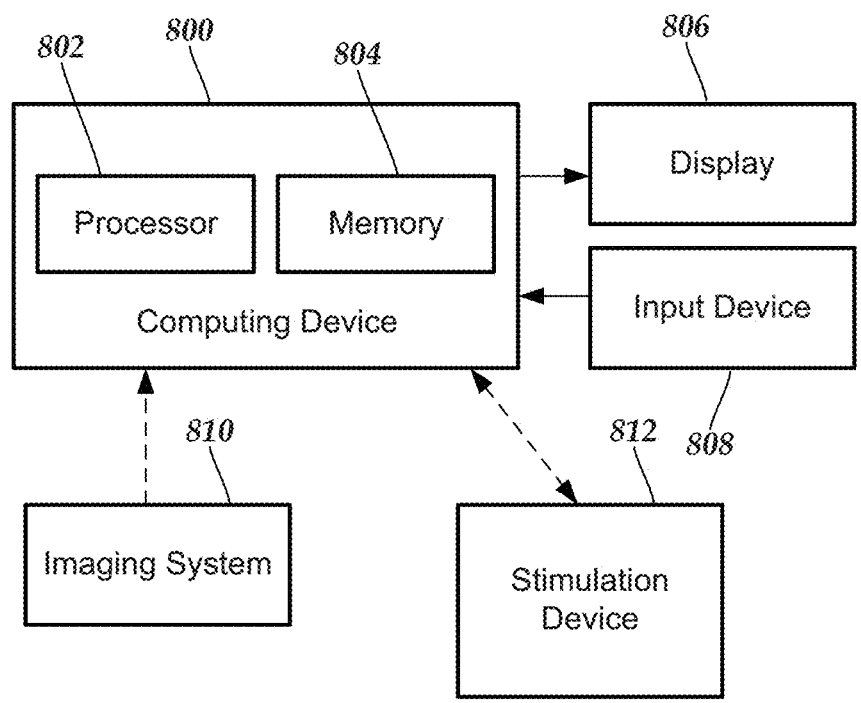
FIG. 8 is a schematic overview of a system for programming or using an electrical stimulation device, according to the invention.

FIG. 8 illustrates one embodiment of a system for practicing the invention. The system can include a computing device 800 or any other similar device that includes a processor 802 and a memory 804, a display 806, an input device 808, and, optionally, a stimulation device 812 (such as an electrical stimulation device or optical stimulation device). The system 800 may also optionally include at least one imaging system 810.

The computing device 800 can be a computer, tablet, mobile device, or any other suitable device for processing information. The computing device 800 can be local to the user or can include components that are non-local to the computer including one or both of the processor 802 or memory 804 (or portions thereof). For example, in at least some embodiments, the user may operate a terminal that is connected to a non-local computing device. In other embodiments, the memory can be non-local to the user.

The computing device 800 can utilize any suitable processor 802 including at least one hardware processors that may be local to the user or non-local to the user or other components of the computing device. The processor 802 is configured to execute instructions provided to the processor 802, as described below.

Any suitable memory 804 can be used for the computing device 802. The memory 804 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has at least one of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 806 can be any suitable display device, such as a monitor, screen, display, or the like, and can include a printer. The input device 808 can be, for example, a keyboard, mouse, touch screen, track ball, joystick, voice recognition system, or any combination thereof, or the like.

At least one imaging system 810 can be used including, but not limited to, MRI, computed tomography (CT), ultrasound, or other imaging systems. The imaging system 810 may communicate through a wired or wireless connection with the computing device 800 or, alternatively or additionally, a user can provide images from the imaging system 810 using a computer-readable medium or by some other mechanism.

The stimulation device 812 can include, for example, any of the components illustrated in FIGS. 1-3C and 5-7 which may include, but is not limited to or required, a control module 102, 102', 710 and one or more leads 103, 503, 603. The stimulation device 812 may communicate with the computing device 800 through a wired or wireless connection or, alternatively or additionally, a user can provide information between the stimulation device 812 and the computing device 800 using a computer-readable medium or by some other mechanism. In at least some embodiments, the computing device 800 may include part of the stimulation device 812, such as, for example, the control module 710, telemetry unit 706, programming unit 708, recharging unit 716, or any combination thereof, or can be a separate device.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

A stimulation system can produce a stimulation effect (such as an electric field, an electrical stimulation field, an electrical field effect, or an optical stimulation effect) that moves spatially over time to produce a desired effect. As an example, an electrical field effect that moves spatially over time can promote or produce cytotaxis of glial cells in the spinal cord and may be used to alleviate pain, reduce inflammation or other effects. Such an arrangement is used herein as an example for describing systems, user interfaces, and methods, but it will be understood that these systems, user interfaces, and methods can be employed for other moving stimulation effects. The system may utilize one or more of the paddle or percutaneous leads described above or any other suitable lead or stimulating arrangement. An optical stimulation system can produce, using optical stimulators, an optical stimulation effect that moves spatially over time to produce a desired effect.

It is thought that cathodes may induce glial migration towards the cathode. Anodes may have an opposite effect to direct glial migration away from the anode. Thus, appropriate selection of cathodes and anodes may direct glial cells away from a site (for example, a nerve injury site where an anode is positioned) and towards a site (for example, a non-injured location where a cathode is positioned.)

Figure 9A:
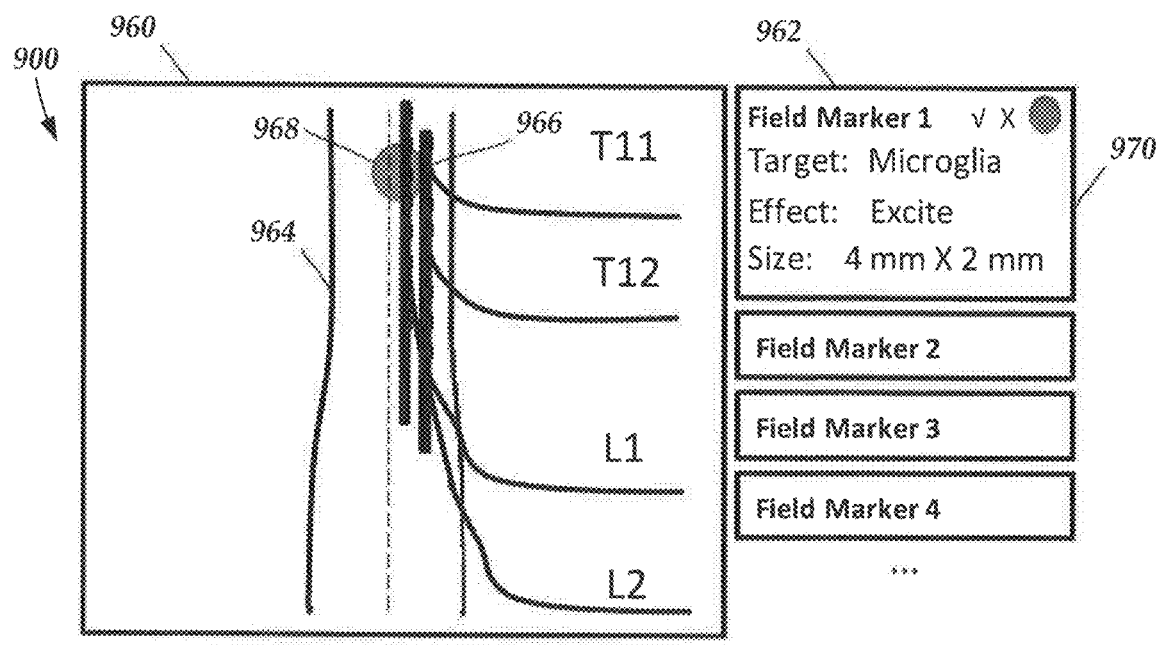
FIG. 9A is a schematic overview of one embodiment of a user interface for planning or conducting stimulation, according to the invention.

FIGS. 9A-9F illustrate user interfaces for a stimulation system that can be provided with, or as part of, computing device 800, control module 710, telemetry unit 706, programming unit 708, recharging unit 716, or any combination thereof, or any other suitable device. FIG. 9A illustrates one embodiment of a user interface 900 that includes a display region 960 and one or more information regions 962.

In the illustrated embodiment, the display region 960 includes an anatomical representation 964, a lead representation 966, and a field representation 968. In the illustrated embodiment, the anatomical representation 964 includes a representation of one or more spinal levels (in FIG. 9A, the thoracic levels T11 and T12 and the lumbar levels L1 and L2) and a representation of spinal nerves exiting the levels, as well as a midline (dotted line) of the spinal cord. It will be understood that other anatomical representations, with more or less detail, can be used or, in some embodiments, a user interface will have no anatomical representation.

In the illustrated embodiment, the lead representation 966 includes portions of one or more leads 903. In the illustrated embodiment, the lead representation includes representations of portions of two percutaneous leads include portions of the lead bodies and the electrodes or optical stimulators. It will be understood that other lead representations, with more or less detail, can be used or, in some embodiments, a user interface will have no lead representation. In at least some embodiments, the user interface may allow the user to place, move, alter, modify or otherwise change or manipulate the lead representation 966. In at least some embodiments, the lead representation 966 may be obtained or determined (or initially determined) from user input or imaging of the implanted lead or leads or other suitable input.

In at least some embodiments, the field representation 968 can be an approximation of the expected field for a selected set of stimulation parameters or may be a target stimulation field for which a set of stimulation parameters are determined by the system or provided by an external system or other source to approximate the target field. Examples of methods and systems for determining stimulation parameters for a target stimulation field can be found at, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; 2015/0066111; 2016/0030749; 2016/0346557; 2016/0375258; 2017/0061627; and 2017/0304633; U.S. patent application Ser. Nos. 15/689, 696; 15/706,004; and Ser. No. 15/783,807; and U.S. Provisional Patent Application Ser. No. 62/444,724, all of which are incorporated herein by reference in their entireties. The selection or determination of electrodes or optical stimulators (or other stimulation parameters) can be provided to a device, such as a control module (for example, control module 102 of FIGS. 1-3A) to for generating the stimulation effect. For example, a control module of an implanted electrical stimulation system can generate the electric field effect using an implanted lead or leads and associated electrodes.

In at least some embodiments, the display region 960 is configured to permit a user to do one or more of the following: place, move, alter, modify, or otherwise change or manipulate the field representation 968. In at least some embodiments, any changes to the field representation 968 may cause the system to determine or otherwise obtain a set of stimulation parameters to approximate the changed field representation.

The information region 962 can include information regarding one or more of the stimulation field, the stimulation parameters, the patient, the anatomy, or any other information related to the stimulation procedure or process. In at least some embodiments, the information in the information region 962 can be entered, altered, modified, or otherwise changed by user input. Such user input may include user entry into a designated space or through selection from menus or otherwise. In at least some embodiments, initial information may be provided as one or more default entries.

In the illustrated embodiment of FIG. 9A, the information region 962 is divided into multiple sections each related to a different "field marker" or field representation 968. FIG. 9A illustrates an expanded section 970 for "Field Marker 1" which corresponds to the illustrated field representation 968. The section 970 includes a number of informational entries or controls. For example, the section 970 includes a "check" for turning on the related field marker and an "X" for turning off the field marker, as well as a representation of the field marker which may be differently colored, shaded, or otherwise graphically distinctive from other field markers (such as Field Marker 2 or Field Marker 3).

The section 970 may include a target selection control. The target selection may be user selected or system selected. Examples of target selections include, but are not limited to, microglia, astrocytes, terminals, axons, neurons, or the like. In at least some embodiments, a particular target selection, such as microglia, can influence or determine stimulation parameters that are determined or otherwise selected by the system including, but not limited to, stimulation frequency (for example, frequencies in the range of 1-10 Hz or 10-500 Hz or 250-1000 Hz or 1 kHz or greater or the like), pulse width (or pulse duration), pulse amplitude, electrode or optical stimulator selection, or the like. In some embodiments, a "custom" target selection may be available which can allow the user more direct control over or selection of stimulation parameters including, but not limited to, stimulation frequency, pulse width (or pulse duration), pulse amplitude, electrode or optical stimulator selection, or the like.

The section 970 may include an effect selection control. The effect selection may be user selected or system selected and may include selection of a type of stimulation effect. Examples of effect selections include, but are not limited to, excite, suppress, inhibit, sub-threshold, or the like. In at least some embodiments, a particular effect selection can influence or determine stimulation parameters that are determined or otherwise selected by the system including, but not limited to, stimulation frequency, pulse width (or pulse duration), pulse amplitude, electrode or optical stimulator selection, or the like.

The section 970 may include a size selection control. The size selection may be user selected or system selected and, at least in some embodiments, may be modified by changes made in the display region 960. In at least some embodiments, a particular size selection can influence or determine stimulation parameters that are determined or otherwise selected by the system including, but not limited to, stimulation frequency, pulse width (or pulse duration), pulse amplitude, electrode or optical stimulator selection, or the like.

Figure 9B:
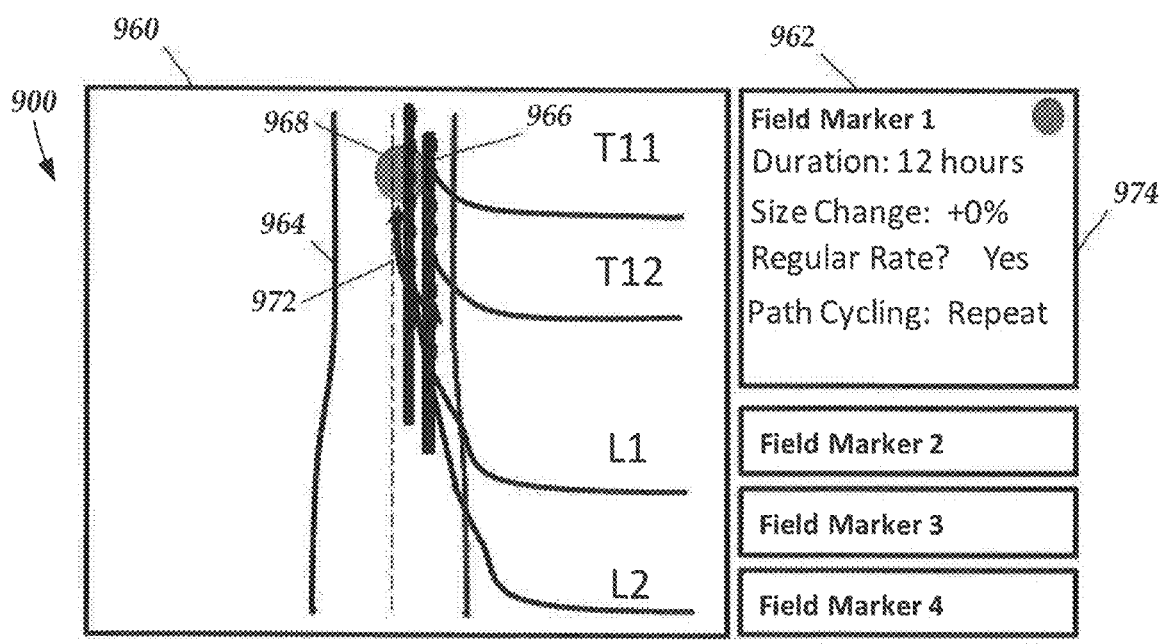
FIG. 9B is a schematic overview of another embodiment of a user interface for planning or conducting stimulation, according to the invention.

FIG. 9B illustrates another embodiment of a user interface 900 that includes a display region 960 and one or more information regions 962. In FIG. 9B, the display region 960 includes a path 972 for migrating a stimulation effect, represented by field representation 968, (or other stimulation effect) and the section 972 of information region 962 includes elements for defining the migrating stimulation effect (such as an electrical field effect). In at least some embodiments, the user interface may allow the user to place, move, alter, modify or otherwise change or manipulate the path 972. In at least some embodiments, the path 972 may be obtained or determined (or initially determined) from user input or by the system or from other suitable input.

The section 974 may include a duration selection control that represents the length of time for the stimulation effect (such as an electrical field effect) to traverse the path 972. The duration selection may be user selected or system selected. In at least some embodiments, the duration selection may be presented in terms of days, hours, minutes, or seconds. In at least some embodiments, a particular duration selection can influence or determine stimulation parameters that are determined or otherwise selected by the system including, but not limited to, stimulation frequency, pulse width (or pulse duration), pulse amplitude, electrode or optical stimulator selection, or the like.

The duration selection can also be related to the path rate or migration rate of glial cells (for example, a migration rate in mm/min). The migration rate may be related to stimulation parameters such as pulse rate, pulse pattern, PW, amplitude, and field size and shape. In at least some instances, the stimulation parameters may influence the release of migration-inducing factors, such as ATP.

The section 974 may include a size change selection control that represents whether or not the field changes in size during traversal of the path 972 and, if so, the type and amount of change. The size change selection may be user selected or system selected. In at least some embodiments, the size change selection may be presented in terms of percentage or absolute size or may use key words or phrases such as "contraction" or "expansion" or the like. In at least some embodiments, a particular size change selection can influence or determine stimulation parameters that are determined or otherwise selected by the system including, but not limited to, stimulation frequency, pulse width (or pulse duration), pulse amplitude, electrode or optical stimulator selection, or the like.

The section 974 may include a change rate selection control that represents whether the rate of change of the stimulation effect (such as an electrical field effect) during the traversal of the path 972 is regular or not. If not regular, a separate input section may be accessed that can be used to configure rates of change over parts of the path 972. The change rate selection may be user selected or system selected. In at least some embodiments, a particular change rate can influence or determine stimulation parameters that are determined or otherwise selected by the system including, but not limited to, stimulation frequency, pulse width (or pulse duration), pulse amplitude, electrode or optical stimulator selection, or the like.

The section 974 may include a cycling selection control that represents whether or not the path 972 is repeated. The cycling selection may be user selected or system selected. In at least some embodiments, the cycling selection may be presented in terms of selections such as "repeat" (path repeats in the same direction each time), "cycle" or "reverse" (field moves sequentially in both directions along the path", "sequence" (allows multiple paths to be defined and traversed in sequence), "shuffle" (allows multiple paths to be defined and traversed in random order), "no repeat", or the like. In at least some embodiments, a particular cycling selection can influence or determine stimulation parameters that are determined or otherwise selected by the system including, but not limited to, stimulation frequency, pulse width (or pulse duration), pulse amplitude, electrode or optical stimulator selection, or the like.

Figure 9C:
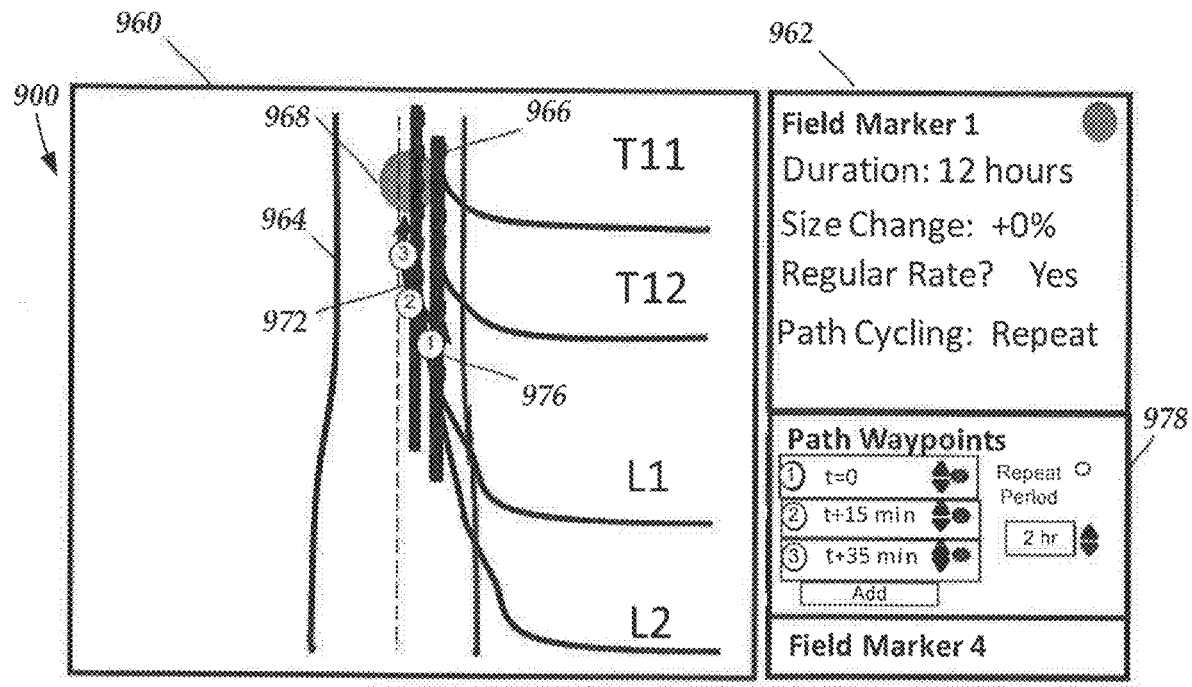
FIG. 9C is a schematic overview of a third embodiment of a user interface for planning or conducting stimulation, according to the invention.

FIG. 9C illustrates another embodiment of a user interface 900 that includes one or more controls for defining waypoints 976 along the path 972. The section 978 of information region 962 includes elements for defining the waypoints 976. In at least some embodiments, the user interface may allow the user to define waypoints in the section 978 or the display region 960, as well as a waypoint time control to define a time (after a starting time t=0) at which the waypoint is to be reached. The user interface may also include one or more controls to allow the user to add or subtract waypoints, to indicate that the path is to be repeated, or to define a repeat period, or any combination thereof. In at least some embodiments, waypoint definition can influence or determine stimulation parameters that are determined or otherwise selected by the system including, but not limited to, stimulation frequency, pulse width (or pulse duration), pulse amplitude, electrode or optical stimulator selection, or the like.

In at least some embodiments, the user interface can include one or more controls to provide an animation of the movement of the field representation 968 along the path 972 in real-time (for example, to show the current field as the stimulation system is operating) or to demonstrate the movement of the field, optionally, in an accelerated manner (for example, showing a cycle taking hours in a minute or less.) In at least some embodiments, the user interface may also indicate which electrodes or optical stimulators are activated during the animation (for example, using graphical markings, highlights or coloring of the electrodes, or "+" and "−" signs or electrode amplitude or fractionalization values.)

Figure 9D:
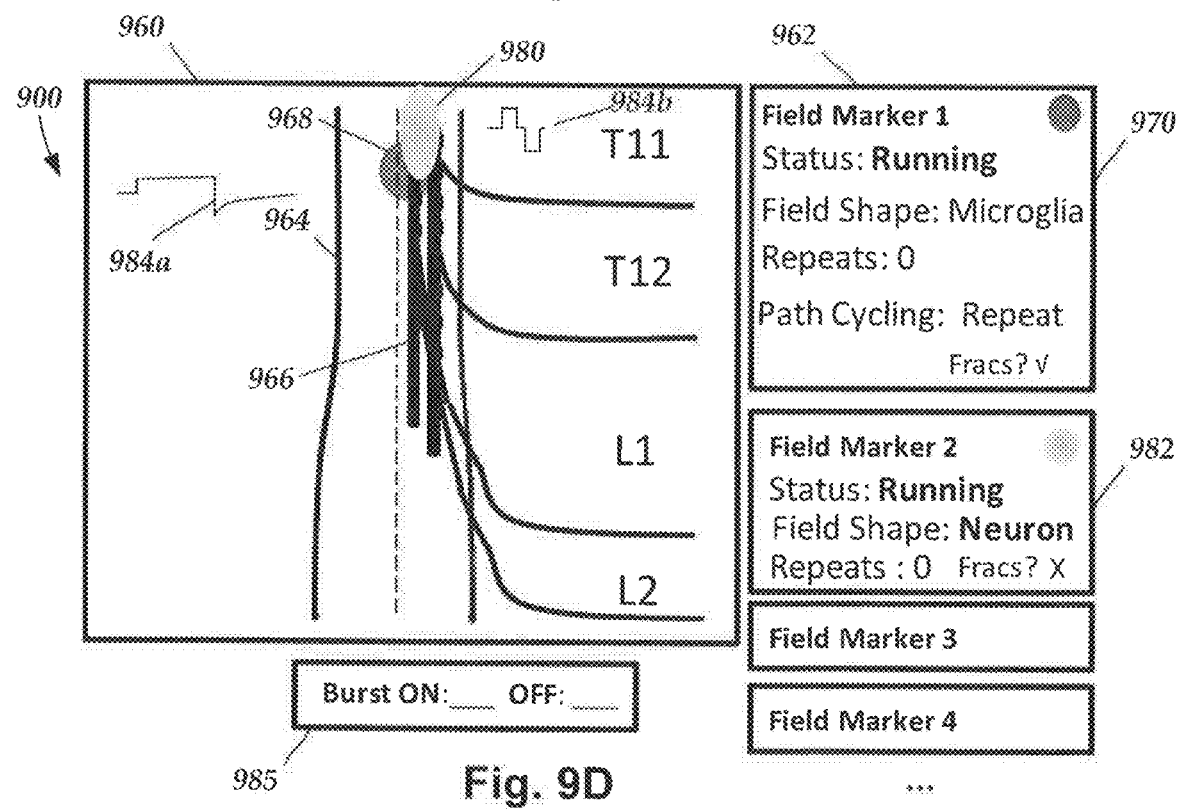
FIG. 9D is a schematic overview of a fourth embodiment of a user interface for planning or conducting stimulation, according to the invention.

Multiple field configurations may be present and definable and could run sequentially, simultaneously, or in any another order. FIG. 9D illustrates a user interface 960 with two fields 968, 980 in the display region 960 and two sections 970, 982 in the information region 962 for defining the fields. In the illustrated embodiment in FIG. 9D, the first field 968 is for stimulating microglia and the second field 980 is for stimulation neurons and follows the first field with the intent of producing a complementary mechanistic effect. The user interface 900 also illustrates a first waveform 984a for the first field 968 and a second waveform 984b for the second field 980. Waveforms may be paired to specific effect(s) and may be visualized or moved with the corresponding field.

Figure 15A:
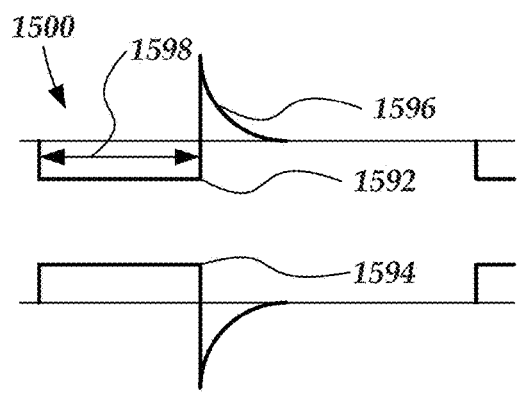
FIG. 15A is a schematic illustration of one embodiment of a waveform for producing an electric field effect, according to the invention.
Figure 15B:
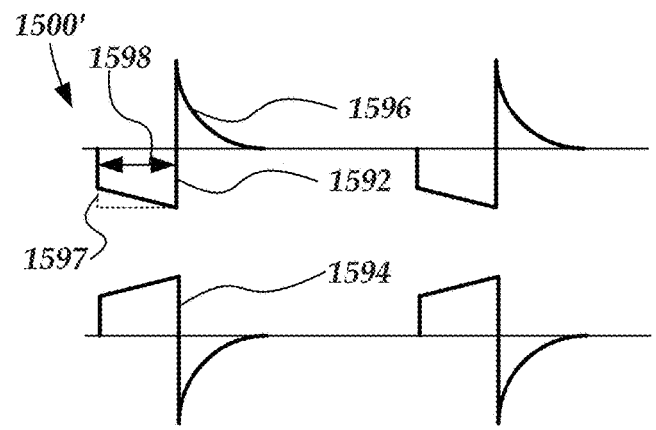
FIG. 15B is a schematic illustration of a second embodiment of a waveform for producing an electric field effect, according to the invention.
Figure 15C:
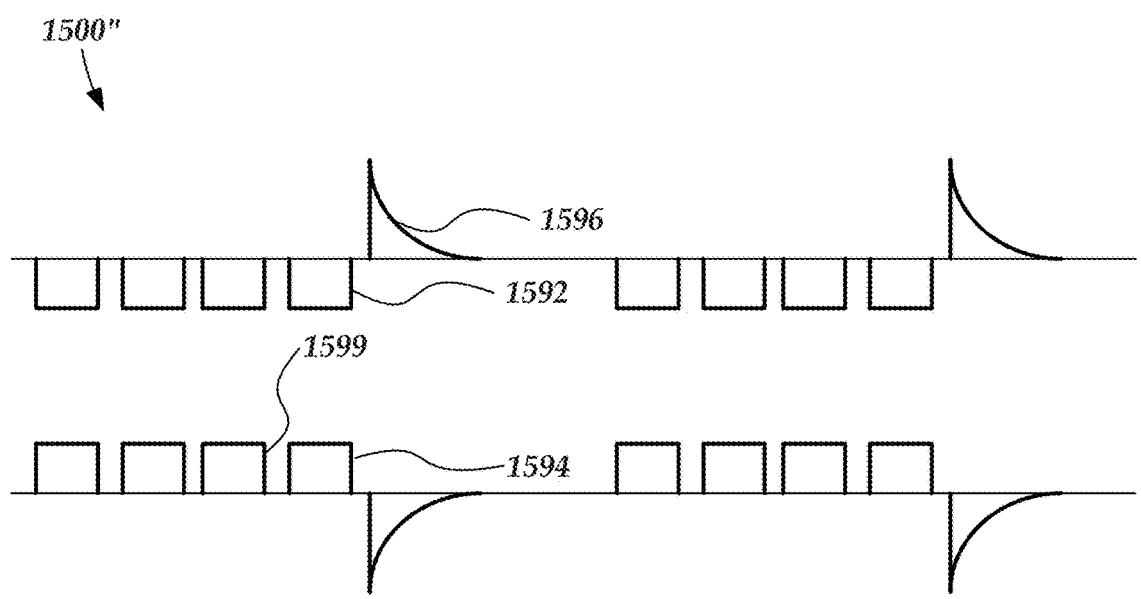
FIG. 15C is a schematic illustration of a third embodiment of a waveform for producing an electric field effect, according to the invention.

FIGS. 15A, 15B, and 15C illustrate examples of waveforms, but it will be understood that other waveforms can be used. The waveform 1500 of FIG. 15A includes both a cathodal waveform 1592 and an anodal waveform 1594 and each of these include an associated charge recovery portion 1596. In at least some embodiments, the waveform 1500 of FIG. 15A has a long pulse width 1598 which may be, for example, at least 1, 2, 3, 4, or 5 milliseconds or longer or may be in a range of 1-10 milliseconds or 1-5 milliseconds.

The waveform 1500' of FIG. 15B includes both a cathodal waveform 1592 and an anodal waveform 1594 and each of these include an associated charge recovery portion 1596. The waveform 1500' has a pulse width 1598. The waveforms 1592 and 1594 have a variable slew rate with a non-zero change in amplitude ($\Delta_{Amp}$) 1597 that corresponds to the difference in the amplitude between the start of the waveform and the end of the waveform. In at least some embodiments, the ratio of $\Delta_{Amp}$ to the final amplitude of the cathodal or anodal waveform 1592, 1594 is at least 0.05, 0.1, 0.15, 0.2, 0.25, 0.3, 0.33, 0.5 or more. In the illustrated embodiment of FIG. 15B, the variation in the slew rate (e.g., the increase in amplitude over time) is linear. In other embodiments, the variation in the slew rate can be exponential, polynomial, or any other suitable function or may vary from being linear, exponential, polynomial or the like by up to 5, 10, 15, 20, 25, 30, or more percent.

The waveform 1500" of FIG. 15C includes both a cathodal waveform 1592 and an anodal waveform 1594 and each of these include an associated charge recovery portion 1596. The cathodal and anodal waveforms 1592, 1594 include multiple bursts 1599 prior to the charge recovery portion. In the illustrated embodiment of FIG. 15C, the cathodal and anodal waveforms 1592, 1594 include four bursts 1599, but any other number of bursts can be used including, but not limited to, two, three, five, six, eight, ten, twelve, or more bursts. Also, as illustrated in FIG. 15C, the charge recovery portion 1596 can be delayed after the cathodal and anodal waveforms 1592, 1594. In at least some embodiments, similar delays can be used with other waveforms including those illustrated in FIGS. 15A and 15B or the charge recovery portion 1596 in FIG. 15C may not be delayed.

In at least some embodiments, field marker numbering can be used to determine priority in case of overlap, order the fields for appearance/delay calculations, control alternation and interleaving. Field "following" characteristics may also be pre-loaded according to disease etiology or target element order or any combination thereof.

FIG. 9D also illustrates a control for another possible stimulation parameter: bursts of pulses. Nerve terminals may become depleted of ATP or other migration inducing diffusible factors, bursting/cycling may be used to maintain effectiveness. A burst or cycle OFF time (or ON time) can be set. In at least some embodiments, the burst or cycle OFF or ON time can be set dynamically based upon feedback (for example, patient pain ratings or sensor signals.)

Signals may be provided from sensors on the lead or implanted sensors external to the lead or sensors external to the patient. The sensor signals can be used for a variety of purposes including, but not limited to, selecting or modifying stimulation parameters, selecting or modifying a path for migration of a stimulation effect (such as an electrical field effect), selecting or modifying cycling of the stimulation field along the path and duration of the cycling or time between cycles, or the like. Examples of chemical signals that may be sensed include, but are not limited to, ATP, BDNF, bFGF, Betaendorphin, Caspace 6, CASP2, Cathepsin S, CCR2, CD11b, CCL2, CCL7, CSF1, CX3XL1, CXCL1, ET, ERK, Frackalkine, GDNF, glutamate, heat shock proteins, IFNalpha, IFNgamma, IL-4, IL-6, IL-10, IL-17, IL-18, IL-33, IL-4, IL-1β, JNK, LE, Lipoxins, MAPK, MMP9, MMP2, NGF, OX-42, P2X4, P2X7, P2Y12, P38-mapK, PGE2, Protectins, Resolvins, TGF-β, TLR-4, TNFalpha, tPA, TSP4, VEGF, WNT3A, WNT5A, or any combination thereof or the like. In at least some embodiments, the system may select or alter stimulation settings based on the sensor signals.

Figure 9E:
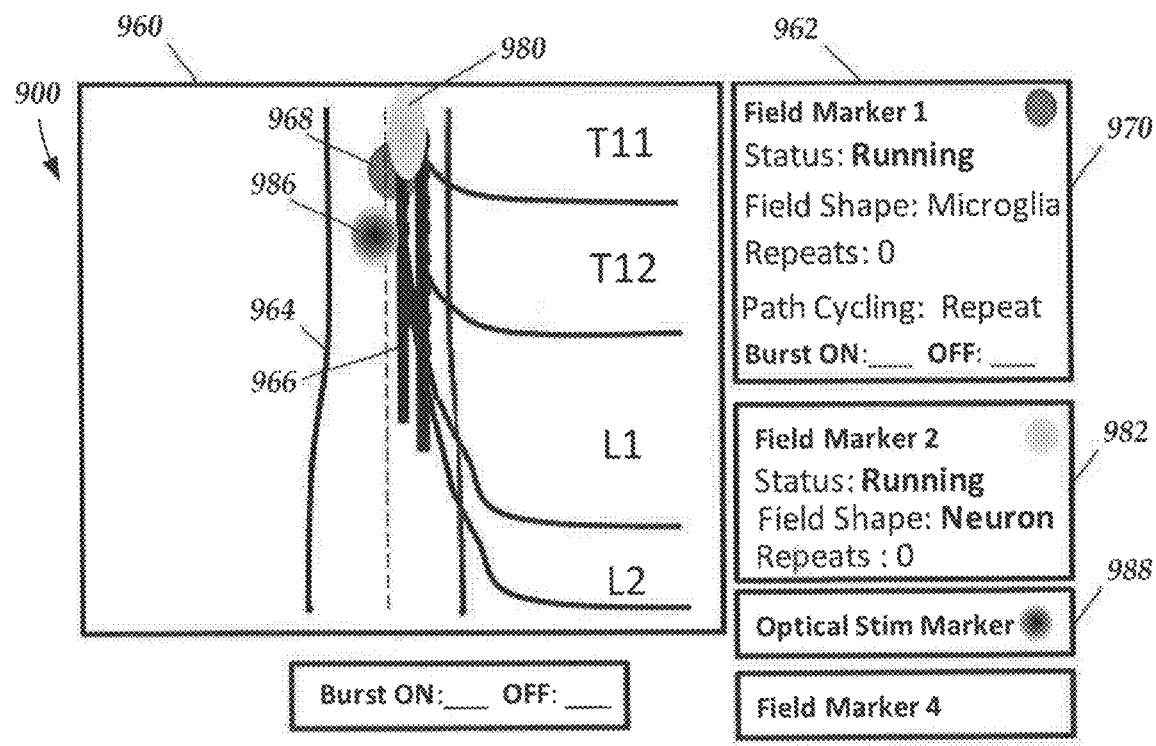
FIG. 9E is a schematic overview of a fifth embodiment of a user interface for planning or conducting stimulation, according to the invention.

FIG. 9E illustrates a user interface 960 with two electrical fields 968, 980 and one optical stimulation region 986 in the display region 960 and two sections 970, 982 in the information region 962 with one or more controls for defining the electrical fields and one section 988 with one or more controls for defining the optical stimulation. If multimodal stimulation (for example, both electrical and optical stimulation) is in effect, fields and stimulation regions may be manually or automatically guided within or around different portions of the anatomy.

Figure 9F:
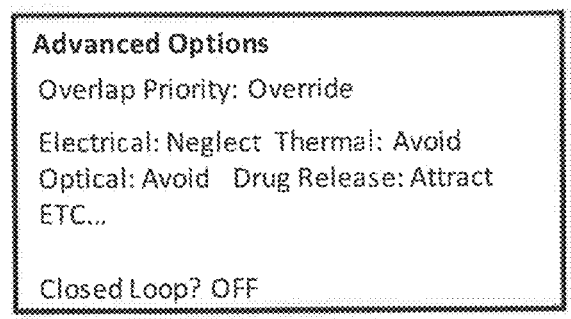
FIG. 9F is a schematic overview of a sixth embodiment of a user interface for planning or conducting stimulation, according to the invention.

FIG. 9F illustrates an information region 962' that can be displayed on the user interface with respect to "Field Marker 1" (or any of the other markers) with one or more controls to define the relationships between the field 968 associated with "Field Marker 1" and any of the other fields or stimulation regions. For example, the first field 968 for microglial stimulation may be automatically configured to avoid overlap with the optical stimulation region 986 as the first field 968 moves along the path 972 (see, FIG. 9B). The information region in FIG. 9F includes one or more controls for selecting overlap effects such as, for example, neglect (for example, do nothing to avoid or enhance overlap), avoid (for example, reduce or eliminate overlap), or attract (for example, promote overlap), or the like. In the illustrated embodiment of FIG. 9F, the field associated with the Field Marker for which the "Advanced Options" are being selected will neglect electrical fields, avoid thermal stimulation regions, avoid optical stimulation region, and be attracted to regions where a drug is released. In at least some embodiments, the path 972 may be automatically or manually modified or guided by sensed electrical, thermal, chemical, optical, or other signals according, for example, to the options selection in the information region of FIG. 9F.

Using the user interfaces, systems, and methods described herein a variety of effects can be obtained. For example, electrode configuration and migration of fields can be used to produce gliomodulatory effects.

Monopolar, bipolar, tripolar, or other multipolar target poles can be selected to facilitate behaviors by microglia, astrocytes, and/or oligodendrocytes to promote healing, reduce inflammation, or relieve pain, or produce any combination of these effects. The cellular behaviors that can be produced include, but are not limited to, electrotaxis, galvanotaxis, chemotaxis, thermogenic effects, and other electromechanical effects such as those produced by Lorentz interactions caused by an applied waveform.

It is thought that Lorentz forces may modulate the release of gliomodulators. For example, monopolar, bipolar, tripolar, or other multipolar target poles can be configured so that the amplitude and orientation of the target pole can induce a directional Lorentz force on glial cells with any morphology. In at least some embodiments, the system may allow a user to define (or the system may automatically define) a target pole, or a set or series of target poles, to induce morphological changes in glial cells that can result in the release of gliomodulators. For example, as described herein, a user interface can permit a user to define a starting field, a path (or one or more spatial vectors), an ending region or end of the path, and a migration rate or path duration, or any combination thereof. In addition, the user interface may permit the user to define whether the path repeats and the rate of repetition. In some embodiments, the target poles may be fit to the existing electrodes using lead squares or other fitting algorithms or methods. The waveform shape or pulse pattern may also be defined to produce the desired glial effect.

In at least some embodiments, monopolar or multipolar configurations can be used to simultaneously produce neuronal and glial effects that act in a complementary manner, such as, for example, a field orientation to produce synaptic activation and a field orientation to promote selective electrotaxis towards or away from a point in the neural structure.

In at least some embodiments, multi-area stimulation (see, for example, FIGS. 9D and 9E) can be used to produce neuronal and glial effects in different regions of the target tissue that may complement each other using the same waveforms (that could be staggered, cycled, or otherwise temporally offset) or different waveforms. For example, spread bipoles in the rostrocaudal direction or strip bipoles in the mediolateral direction or any combination thereof can be effective and may be selected to avoid or provide relatively little neuronal stimulation. In at least some embodiments, migratory fields can be used where distinct sets of contacts along the lead are successively activated over fixed or variable intervals to deliver a specific phase of a given waveform, pulse pattern, of the like to a specific part of the region of interest and migrated in a way to encourage electrotaxis.

In addition to, or as an alternative to, defining spatial elements of the stimulation, temporal elements of the stimulation can also be defined. For example, a pulse frequency (for example, in a range of 2 Hz to 10 kHz), a pulse width (for example, in range of 10 microseconds to 1 millisecond or more), an amplitude (for example, in a range of 0.1 to 25 mA or more), or a pulse shape (for example, square, sawtooth, sinusoidal, or any other suitable shape including user-define or template shapes that can be regular or irregular), or any combination of these features can be user-defined or system-defined.

As an example, long pulse width, low slew rate waveforms over several contacts can be scheduled in order to evoke gradual migration of glial populations to/from regions of the spinal cord. It is thought, for example, that long pulse width, low slew rate waveforms may depolarize the synapse and also induce a desired glial effect such as electro- or chemo-taxis, or glially mediated changes in synaptic strength (for example, via neurotransmitter binding to sites on glia, modulation of calcium dynamics).

The user interface, or the system, may allow program schedules to be built for a patient, optionally based on patient-acquired data, or downloaded (or otherwise obtained) from a database. In at least some embodiments, these program schedules may be configurable by the user (e.g., a programmer, clinician, or patient.) The program schedule may cycle between sets of waveforms or patterns or other parameters (or any combination of parameters) over time. This cycling may be pre-determined or may be modified by a user or the system to produce a desired effect. Prolonged gliomodulation may result in depletion of gliotransmitters. Such an effect may be mitigated, and energy use may be reduced by cycling stimulation (for example, cycling based upon known or derived glial depletion curves).

In at least some embodiments, a noise signal may be delivered on top of another waveform (for example a square, sawtooth, or sinusoidal waveform) to encourage stochastic resonance. This may provide a subthreshold enhancement of a desired electric field or stimulation effect at a suprathreshold level. For example, a low amplitude waveform could be applied simultaneously with a higher amplitude waveform to produce a sub-threshold effect, such as glial electromechanical modulation that enhances or makes supra-threshold an effect due to the presence of the higher amplitude waveform that would otherwise not have occurred. In at least some embodiments, the low- and high-amplitude waveforms may be designed based on a model or machine learning from clinical data for producing complementary neuron-glial effects. In at least some embodiments, random pulses may be interspersed onto a regular waveform to produce subthreshold effects on neurons or glia or any combination thereof that may, upon introduction of a regular pulse, produce or enhance a desired effect.

In at least some embodiments, the system may be arranged to produce multimodal gliomodulation combining two or more of electrical, optical, thermal, acoustic, or chemical stimulation.

FIG. 10 illustrates one embodiment of a method of planning or conducting stimulation. In step 1002, a user interface displays a representation of stimulation effect (such as an electrical field effect) see, for example, FIGS. 9A and 9B. Parameters for describing the stimulation effect or the size and shape of the stimulation effect can be selected manually or automatically. In step 1004, a path for migration of the stimulation effect is obtained and displayed (see, for example, FIG. 9B.) In at least some embodiments, the path can be received or otherwise obtained from a user through user input. In at least some embodiments, a path may be determined automatically or semi-automatically by a system or processor using any suitable method including, but not limited to, image recognition, machine learning, artificial intelligence, or the like. In step 1006, a duration or rate for migration of the stimulation effect is received. In step 1008, the system or user (or any combination thereof) determines a selection of one of more electrodes or optical stimulators for one or more stimulation leads of a stimulation system to produce the stimulation effect (such as an electrical field effect) and conduct the migration of the stimulation effect along the path according to the duration or rate. This determination may be automatic or manual and, at least in some embodiments, the selection of electrodes or optical stimulators may be modifiable by the user or system (for example, to avoid other defined stimulation effects or optical or thermal stimulation zones or the like, as described above.) If more than one stimulation effect is desired, steps 1002-1008 (or any subset of these steps) can be repeated for each stimulation effect.

In optional step 1010, the selection of electrodes or optical stimulators (or other stimulation parameters) can be provided to a device, such as a control module (for example, control module 102 of FIGS. 1-3A) to for generating the stimulation effect. For example, a control module of an implanted electrical stimulation system can generate an electric field effect using an implanted lead or leads and associated electrodes.

FIG. 11 illustrates one embodiment of a method of defining a path for migration of a stimulation effect (such as an electrical field effect). In step 1102, one or more waypoints are selected or otherwise defined (see, for example, FIG. 9C). In step 1104, optionally, a time is selected to reach each of the waypoints (see, for example, FIG. 9C).

Figure 12:
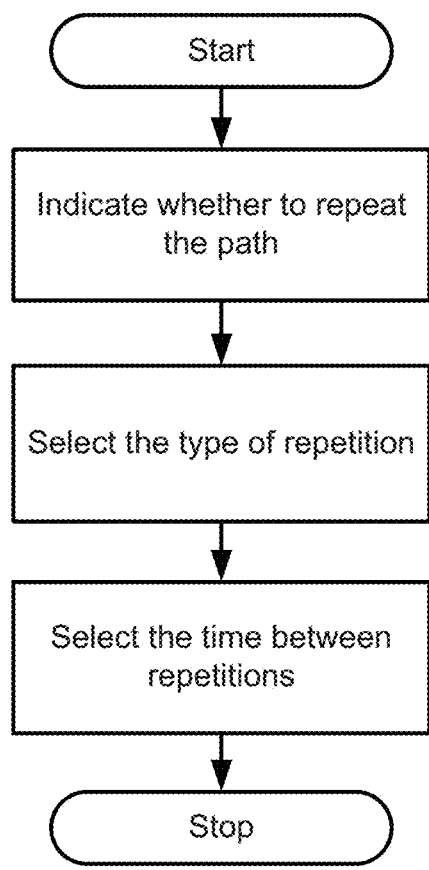
FIG. 12 is a flowchart of one embodiment of a method for defining repetition of a path for migration of a stimulation effect, according to the invention.

FIG. 12 illustrates one embodiment of a method of defining repetition of a path for migration of a stimulation effect (such as an electrical field effect). In step 1202, the user or system indicates whether to repeat the path. In optional step 1204, the user or system selects a type of repetition such as, for example, "repeat" (path repeats in the same direction each time), "cycle" or "reverse" (field moves sequentially in both directions along the path", "sequence" (allows multiple paths to be defined and traversed in sequence), "shuffle" (allows multiple paths to be defined and traversed in random order), "no repeat", or the like. In optional steps 1206, the user or system selects a time between repetitions. For example, the time can be a time between the end of one cycle along the path and the start of the next cycle along the path or the time can be a time between the start of one cycle and the start of the next cycle.

Figure 13:
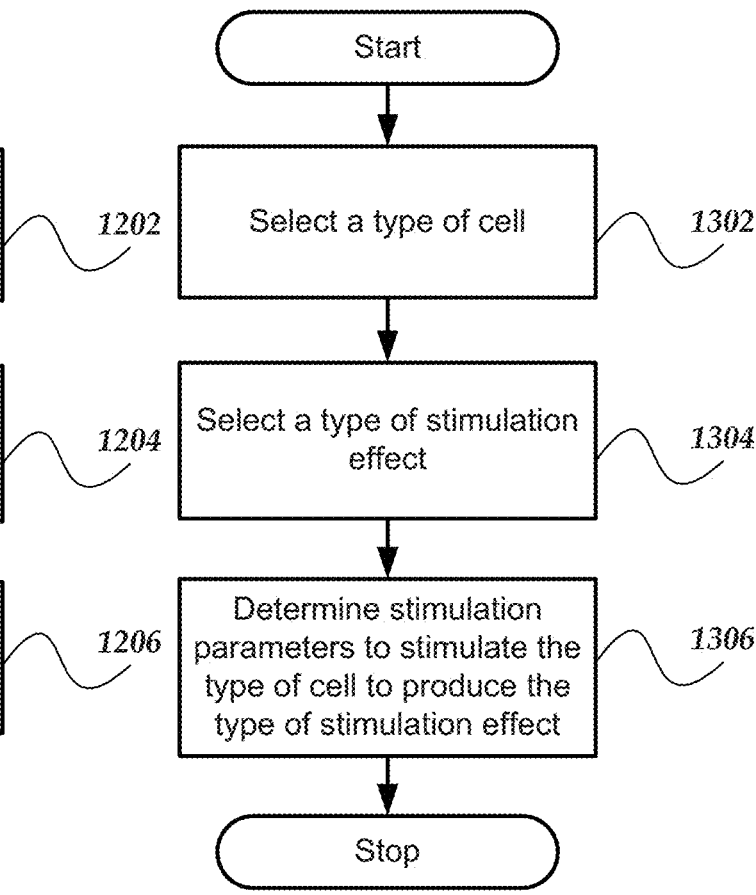
FIG. 13 is a flowchart of one embodiment of a method for defining stimulation of a particular type of cell to achieve a particular effect, according to the invention.

FIG. 13 illustrates one embodiment of a method of defining a particular type of cell to achieve a particular stimulation effect. In step 1302, a type of cell is automatically or manually selected. For example, the type of cell can be microglia, astrocytes, terminals, axons, neurons, or the like. In step 1304, a type of simulation effect is selected. For example, the type of stimulation effect can be excite, suppress, inhibit, sub-threshold, or the like. In optional step 1306, one or more stimulation parameters (for example, electrode or optical stimulator selection, stimulation amplitude, pulse width, pulse duration, whether to burst, time between pulses, pulse waveform, or the like) can be selected or determined to stimulate the type of cell to produce the effect.

Figure 14:
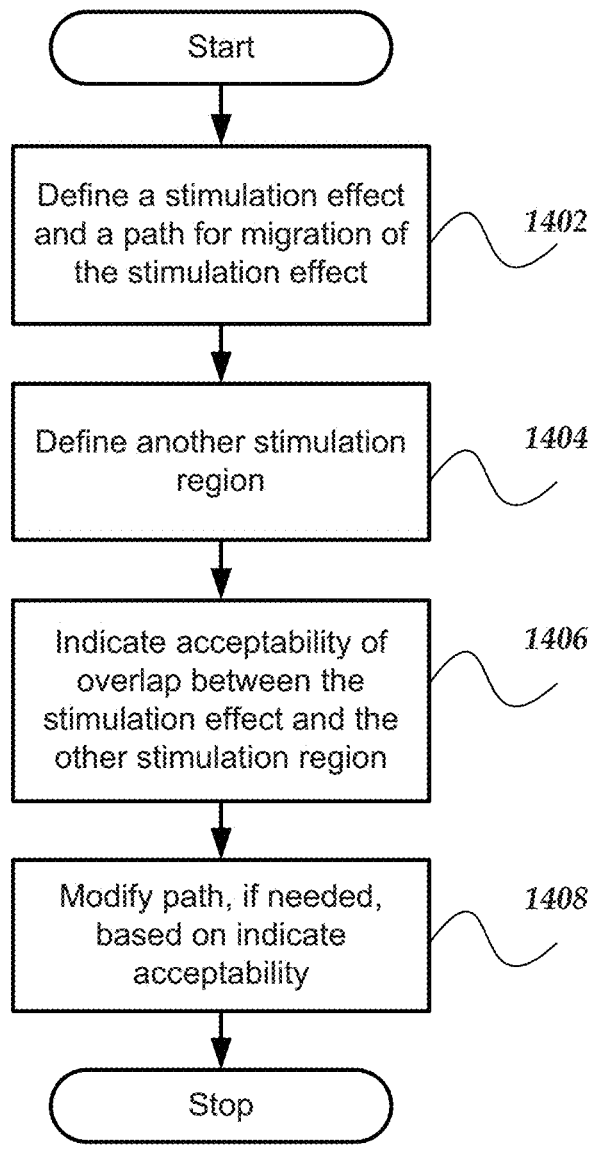
FIG. 14 is a flowchart of another embodiment of a method for planning or conducting stimulation, according to the invention.

FIG. 14 illustrates one embodiment of a method of planning and conducting stimulation. In step 1402, a stimulation effect (such as an electrical field effect) and a path for migration of the stimulation effect is defined (see, for example, FIGS. 9A-9C and 10). In step 1404, another stimulation region, such as an optical, thermal, or chemical stimulation region is defined (see, for example, FIG. 9E). In step 1406, acceptability of overlap between the stimulation effect and other stimulation region is automatically or manually selected or otherwise indicated (see, for example, FIG. 9F). Examples of overlap effects can be overlap effects such as, for example, neglect (for example, do nothing to avoid or enhance overlap), avoid (for example, reduce or eliminate overlap), or attract (for example, promote overlap), or the like. In optional step 1408, the path may be modified, if needed or desired, based on the indicate acceptability. For example, the path may be modified to reduce or eliminate overlap if the overlap is indicated as "avoid".

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, at least one process may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

A system can include one or more processors that can perform the methods (in whole or in part) described above. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process. In at least some embodiments, the processor may include more than one processor.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A system for producing cytotaxis of glial cells along a path for migration, the system comprising:
    a display; and
    a processor that executes instructions configured for:
        displaying, on the display, a representation of a stimulation effect, wherein the stimulation effect comprises the production of cytotaxis of glial cells along the path for migration by sequential generation of electrical stimulation along the path for migration;
        obtaining and displaying, on the display, a graphical representation of the path for migration of the stimulation effect;
        receiving a duration or rate for migration of the stimulation effect along the path; and
        determining a selection of one or more electrodes or optical stimulators for one or more stimulation leads of a stimulation system to sequentially generate electrical stimulation along the path for migration to produce the stimulation effect and conduct the migration of the stimulation effect along the path according to the duration or rate.

2. The system of claim 1, wherein the stimulation effect comprises an effect resulting from an electrical stimulation field.

3. The system of claim 1, wherein the stimulation effect comprises an effect resulting from an optical stimulation field.

4. The system of claim 1, wherein the instructions are further configured for receiving an indication of whether to repeat migration of the stimulation effect along the path.

5. The system of claim 1, wherein the instructions are further configured for initiating a signal to deliver the selection of the one or more electrodes or optical stimulators to a stimulation system to generate the stimulation effect for delivery to a patient.

6. The system of claim 1, wherein the instructions are further configured for receiving an indication of whether to repeat migration of the stimulation effect in a reverse direction along the path.

7. The system of claim 1, wherein the instructions are further configured for receiving a plurality of waypoints along the path.

8. The system of claim 7, wherein the instructions are further configured for receiving a time or rate for each of the plurality of waypoints.

9. The system of claim 1, wherein the instructions are further configured for receiving a stimulation target, wherein the stimulation target is a type of glial cell.

10. The system of claim 1, wherein the instructions are further configured for receiving a size change parameter describing a change in a size of the stimulation effect as the stimulation effect migrates along the path.

11. The system of claim 1, wherein the instructions are further configured for displaying, on the display, a representation of a neuronal stimulation field.

12. The system of claim 1, wherein the instructions are further configured for
    displaying, on the display, a representation of another stimulation field;
    receiving an indication regarding acceptability of overlap between the other stimulation field and the stimulation effect during migration of the stimulation effect along the path; and
    modifying the path to reduce or avoid the overlap between the other stimulation field and the stimulation effect.

13. The system of claim 1, wherein the instructions are further configured for presenting a user interface on the display, the user interface comprising:
    the representation of the stimulation effect;
    a path control configured to receive input of the path for migration of the stimulation effect.

14. The system of claim 13, wherein the user interface further comprises a cycling control configured to select whether the path is repeated in a same direction or in a reverse direction.

15. The system of claim 13, wherein the user interface further comprises a duration control for selecting a duration of the migration of the stimulation effect along the path.

16. The system of claim 13, wherein the user interface further comprises a lead representation of at least one stimulation lead configured for electrical stimulation, optical stimulation, or both.

17. A non-transitory processor readable storage media that includes instructions for producing cytotaxis of glial cells along a path for migration wherein execution of the instructions by one or more processor devices performs actions, comprising:
    displaying, on a display, a representation of a stimulation effect, wherein the stimulation effect comprises the production of cytotaxis of glial cells along the path for migration by sequential generation of electrical stimulation along the path for migration;
    obtaining and displaying, on the display, a graphical representation of the path for migration of the stimulation effect;
    receiving a duration or rate for migration of the stimulation effect; and
    determining a selection of one of more electrodes or optical stimulators for one or more stimulation leads of a stimulation system to sequentially generate electrical stimulation along the path for migration to produce the stimulation effect and conduct the migration of the stimulation effect along the path according to the duration or rate.

18. The non-transitory processor readable storage media of claim 17, wherein the actions further comprise receiving an indication of whether to repeat migration of the stimulation effect in a reverse direction along the path.

19. A method for producing cytotaxis of glial cells along a path for migration, the method comprising:
- displaying, on a display, a representation of a stimulation effect, wherein the stimulation effect comprises the production of cytotaxis of glial cells along the path for migration by sequential generation of electrical stimulation along the path for migration;
- obtaining and displaying, on the display, a graphical representation of the path for migration of the stimulation effect;
- receiving a duration or rate for migration of the stimulation effect; and
- determining a selection of one of more electrodes or optical stimulators for one or more stimulation leads of a stimulation system to sequentially generate electrical stimulation along the path for migration to produce the stimulation effect and conduct the migration of the stimulation effect along the path according to the duration or rate.

20. The method of claim 19, further comprising receiving a plurality of waypoints along the path.

\* \* \* \* \*